United States Patent
Bartlett

(10) Patent No.: US 11,278,628 B2
(45) Date of Patent: *Mar. 22, 2022

(54) PHARMACEUTICAL FORMULATIONS AND METHODS OF USE THEREOF

(71) Applicant: ImmunoGen, Inc., Waltham, MA (US)

(72) Inventor: Elizabeth Bartlett, Charlemont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 140 days.

This patent is subject to a terminal disclaimer.

(21) Appl. No.: 16/680,930

(22) Filed: Nov. 12, 2019

(65) Prior Publication Data

US 2020/0222552 A1    Jul. 16, 2020

Related U.S. Application Data

(63) Continuation of application No. 16/458,987, filed on Jul. 1, 2019, now abandoned, which is a continuation of application No. 15/360,689, filed on Nov. 23, 2016, now abandoned.

(60) Provisional application No. 62/368,156, filed on Jul. 28, 2016, provisional application No. 62/260,104, filed on Nov. 25, 2015.

(51) Int. Cl.
| | |
|---|---|
| *C07K 16/28* | (2006.01) |
| *A61K 39/395* | (2006.01) |
| *A61K 47/18* | (2017.01) |
| *A61K 31/5517* | (2006.01) |
| *A61K 47/26* | (2006.01) |
| *A61K 47/68* | (2017.01) |
| *C07D 519/00* | (2006.01) |
| *A61K 9/00* | (2006.01) |
| *A61K 47/12* | (2006.01) |

(52) U.S. Cl.
CPC ........ *A61K 47/6803* (2017.08); *A61K 9/0019* (2013.01); *A61K 31/5517* (2013.01); *A61K 39/39591* (2013.01); *A61K 47/12* (2013.01); *A61K 47/183* (2013.01); *A61K 47/186* (2013.01); *A61K 47/26* (2013.01); *A61K 47/6849* (2017.08); *C07D 519/00* (2013.01); *C07K 16/28* (2013.01); *C07K 16/2803* (2013.01); *C07K 16/2866* (2013.01); *C07K 2317/24* (2013.01); *C07K 2317/56* (2013.01); *C07K 2317/565* (2013.01)

(58) Field of Classification Search
CPC .............. C07D 519/00; A61K 31/5517; A61K 47/6803; C07K 16/2866
See application file for complete search history.

(56) References Cited

U.S. PATENT DOCUMENTS

| | | | | |
|---|---|---|---|---|
| 10,077,313 | B2 * | 9/2018 | Kovtun | ................... A61P 35/02 |
| 10,442,865 | B2 * | 10/2019 | Kovtun | ................... A61P 35/00 |
| 10,875,925 | B2 * | 12/2020 | Kovtun | .............. A61K 47/6883 |
| 10,919,969 | B2 * | 2/2021 | Kovtun | ................... A61P 35/00 |
| 2006/0002942 | A1 | 1/2006 | Kunz et al. | |
| 2006/0246004 | A1 | 11/2006 | Adams et al. | |
| 2012/0009181 | A1 | 1/2012 | Ab | |
| 2012/0009199 | A1 | 1/2012 | Dimitrova et al. | |
| 2012/0238731 | A1 | 9/2012 | Fishkin et al. | |
| 2014/0314781 | A1 | 10/2014 | Krause et al. | |
| 2014/0369924 | A1 | 12/2014 | Weissman et al. | |
| 2017/0014522 | A1 | 1/2017 | Yoder et al. | |
| 2017/0029514 | A1 | 2/2017 | Kovtun et al. | |

FOREIGN PATENT DOCUMENTS

| | | | |
|---|---|---|---|
| WO | 2005042029 | A2 | 5/2005 |
| WO | 2008079290 | A2 | 7/2008 |
| WO | 2009002521 | A2 | 12/2008 |
| WO | 2011130598 | A1 | 10/2011 |
| WO | 2012112687 | A1 | 8/2012 |
| WO | 2012112708 | A1 | 8/2012 |
| WO | 2012128868 | A1 | 9/2012 |
| WO | 2014191560 | A1 | 12/2014 |
| WO | 2017004025 | | 1/2017 |
| WO | 2017004026 | | 1/2017 |

OTHER PUBLICATIONS

International Search Report and Written Opinion of the International Searching Authority, dated Apr. 10, 2017, PCT/US16/63624, ISA/US, pp. 1-16.
Paul, Fundamental Immunology, 3rd Edition, 1993, pp. 292-295, under the heading "Fv Structure and Diversity in Three Dimensions".
Colman, Research in Immunology, 145:33-36, 1994.
Rudkoff et al., Proc. Natl. Acad. Sci. USA 79(6):1979-1983, Mar. 1982.
Khantasup et al., Monoclonal Antibodies in Immunodiagnosis and Immunotherapy, 2015, 34(6): 404-417.
Bendig, Methods: A Companion to Methods in Enzymology, 1995; 8:83-93.

* cited by examiner

*Primary Examiner* — Hong Sang
(74) *Attorney, Agent, or Firm* — Nixon & Vanderhye, PC

(57) ABSTRACT

This disclosure is directed to antibody-drug conjugates. More specifically, this disclosure is directed to compositions comprising (i) antibody-drug conjugates comprising benzodiazepines, and (ii) a small hydrophobic molecule, methods of treatment using the compositions, and methods of formulating the compositions. Furthermore, this disclosure is directed to methods of reducing reversible self-association in antibodies and in antibody-drug conjugates.

16 Claims, 11 Drawing Sheets
Specification includes a Sequence Listing.

PHARMACEUTICAL FORMULATIONS AND METHODS OF USE THEREOF

PRIORITY CLAIM

This application is a continuation application of co-pending U.S. application Ser. No. 16/458,987, filed Jul. 1, 2019, which is a continuation application of U.S. application Ser. No. 15/360,689, filed Nov. 23, 2016, which claims priority to U.S. Provisional Application No. 62/368,156, filed Jul. 28, 2016, and to U.S. Provisional Application No. 62/260,104, filed Nov. 25, 2015. The entire disclosures of those applications are incorporated herein by reference.

SEQUENCE LISTING

The instant application contains a Sequence Listing which has been submitted electronically in ASCII format and is hereby incorporated by reference in its entirety. Said ASCII copy, created on Dec. 14, 2016, is named P155_US003_SL.txt and is 22,322 bytes in size.

FIELD

The present disclosure relates to pharmaceuticals. More specifically, this disclosure relates to formulations for antibody-drug conjugates and methods related to antibody-drug conjugate compositions.

BACKGROUND

In recent years, the treatment of cancer has become more targeted through the development of antibody-drug conjugates (herein referred to as "ADCs," "conjugates," or "immunoconjugates"). Researchers have identified and taken advantage of cell-surface receptors and antigens selectively expressed by cancer cells to develop drugs based on antibodies that bind tumor-specific or tumor-associated antigens. This specific binding allows for the delivery to the cancer cells of cytotoxic compounds linked to the antibody. The selectivity afforded by ADCs minimizes toxicity to normal cells, thereby enhancing tolerability of the drug in the patient.

Despite the tumor selectivity afforded by ADCs, the use of ADCs in a clinical context is limited by a number of factors. Among those factors is the ability of the ADCs to aggregate and reversibly self-associate. ADCs are able to aggregate to each other through various mechanisms, including covalent bonding and hydrophobic interactions. ADCs are also able to reversibly self-associate through weak interactions that create equilibrium between monomers and higher ordered species. In either case, aggregation and reversible self-association inhibit the ability of the ADC to bind to the target, thereby reducing the clinical efficacy of the ADC. Accordingly, researchers continue to work to discover ways to limit aggregation and reversible self-association of the ADCs and increase the efficacy of ADCs.

SUMMARY

This disclosure is directed to ADC compositions with reduced reversible self-association, methods of treating cancer using such compositions, methods of formulating such compositions, and methods of reducing reversible self-association. In one aspect, this disclosure provides a composition comprising (a) an ADC comprising at least one benzodiazepine; and (b) a small hydrophobic molecule selected from the group consisting of betaines and amino acids with hydrophobic side chains. In some embodiments, the composition has a pH between about 4.0 and about 4.5. In some embodiments, the benzodiazepine is an indolinobenzodiazepine. In some embodiments, the benzodiazepine is selected from the group consisting of D1, D1(a), D2, D2(a), DGN462, DGN462(a), D3, D3(a), D4, D4(a), D5, D5(a), D6, and D6(a), which are described below in Table 1. In certain embodiments, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3(a), Ab-sSPDB-D4, Ab-sSPDB-D4(a), Ab-Cys-D1, Ab-Cys-D1(a), Ab-Ser-D1, Ab-Ser-D1(a), Ab-Cys-DGN462, Ab-Cys-DGN462(a), Ab-Ser-DGN462, Ab-Ser-DGN462(a), Ab-Cys-D5, Ab-Cys-D5(a), Ab-Ser-D6, and Ab-Ser-D6(a), which are described below in Table 2. In some embodiments, the composition is an aqueous solution.

In some embodiments, the antibody is selected from the group consisting of huMy9-6, huB4, huDS6, huMov19, and huCD37-3. In other embodiments, the antibody is a humanized CD123 antibody. In certain embodiments, the antibody is a humanized CD123 antibody described in U.S. Provisional application No. 62/186,161, U.S. Patent Application Publication No. US20170029514A1, and PCT Application publication no. WO2017004026, which are herein incorporated by reference in their entireties. As used herein, "AbX" refers to humanized CD123 antibodies described in U.S. Provisional Application No. 62/186,161, U.S. Patent Application Publication No. US20170029514A1, and PCT Application publication no. WO2017004026. All applications, patents, and other publications referenced herein are incorporated by reference. In some embodiments, the AbX antibody comprises the CDR sequences disclosed herein. In some embodiments, the AbX antibody comprises the heavy chain variable region domain sequences and light chain variable region domain sequences disclosed herein.

In further embodiments, the composition is a lyophilized composition. In still further embodiments, the composition is a reconstituted lyophilized composition. Although the small hydrophobic molecule can be added to compositions prior to lyophilization, the benefits of reduced or inhibited reduced reversible self-association are still realized in compositions that are reconstituted after lyophilization.

In some embodiments, the small hydrophobic molecule is trimethylglycine. In certain embodiments, the small hydrophobic molecule is proline. In other embodiments, the small hydrophobic molecule is leucine. In further embodiments, the small hydrophobic molecule is isoleucine. In still further embodiments, two or more small hydrophobic molecules are used in combination in the compositions.

The number of benzodiazepines per antibody in an ADC can vary. In some embodiments, the ADC comprises at least one benzodiazepine. In certain embodiments, the ADC comprises at least two benzodiazepines. In further embodiments, the ADC comprises at least three benzodiazepines. In still further embodiments, the ADC comprises at least four benzodiazepines. In other embodiments, the ADC comprises at least five benzodiazepines. In certain embodiments, the ADC comprises at least six benzodiazepines. In some embodiments, the ADC comprises about seven benzodiazepines. In compositions comprising more than one ADC, the average number of benzodiazepines per antibody can be measured. This number is referred to as the drug-to-antibody ratio, or "DAR." In some embodiments, a composition comprising more than one ADC has a DAR between about 1 and about 4. In some embodiments, a composition comprising more than one ADC has a DAR between 0 and about 1. In other embodiments, a composition comprising more than one ADC has a DAR between about 1 and about 2. In still other embodiments, a composition comprising more than one ADC has a DAR between about 2 and about 3. In further embodiments, a composition comprising more than one ADC has a DAR of between about 3 and about 4. In still further embodiments, a composition comprising more than one ADC has a DAR between about 4 and about 5. In yet further embodiments, a composition comprising more than one ADC has a DAR between about 5 and about 6. In some embodiments the benzodiazepine is conjugated to the antibody in a site-specific manner, for example, through conjugation to an engineered cysteine or serine residue.

In some embodiments, the composition is an aqueous formulation comprising: (a) water; (b) huMy9-6-sSPDB-DGN462; (c) 10 mM sodium succinate; and (d) 280 mM betaine, wherein the formulation has a pH of about 4.2. In another embodiment, the composition is an aqueous formulation comprising: (a) water; (b) huMy9-6-sSPDB-DGN462; (c) 10 mM sodium succinate; and (d) 280 mM proline, wherein the formulation has a pH of about 4.2. In yet another embodiment, the composition is an aqueous formulation comprising: (a) water; (b) AbX-D2; (c) 10 mM sodium succinate; and (d) a small hydrophobic molecule selected from the group consisting of 280 mM proline and 280 mM betaine, wherein the formulation has a pH of about 4.2. In one embodiment, the composition is an aqueous formulation comprising: water; (a) huMov19-sSPDB-D1; (b) 10 mM sodium succinate; and (c) 125 mM leucine, wherein the formulation has a pH of about 4.2. In another embodiment, the composition is an aqueous formulation comprising: (a) water; (b) huMov19-sSPDB-D4; (c) 10 mM sodium succinate; and (a) 125 mM isoleucine, wherein the formulation has a pH of about 4.2. In some embodiments, the composition is a lyophilized composition of any of the aqueous compositions described herein.

In another aspect, the disclosure provides a method of treating cancer in a subject, comprising administering to a subject in need thereof an effective amount of a composition comprising (i) an ADC comprising a benzodiazepine; and (ii) a small hydrophobic molecule selected from the group consisting of betaines and amino acids with hydrophobic side chains, wherein the ADC is cytotoxic in one or more cells, thereby treating the cancer. In some embodiments, the composition is a lyophilized composition. In certain embodiments, the composition is a reconstituted lyophilized composition. In some embodiments of the method, the benzodiazepine is selected from the group consisting of D1, D1(a), D2, D2(a), DGN462, DGN462(a), D3, D3(a), D4, D4(a), D5, D5(a), D6, and D6(a). In certain embodiments, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3(a), Ab-sSPDB-D4, Ab-sSPDB-D4(a), Ab-Cys-D1, Ab-Cys-D1(a), Ab-Ser-D1, Ab-Ser-D1(a), Ab-Cys-DGN462, Ab-Cys-DGN462(a), Ab-Ser-DGN462, Ab-Ser-DGN462(a), Ab-Cys-D5, Ab-Cys-D5(a), Ab-Ser-D6, and Ab-Ser-D6(a). In some embodiments, the antibody (Ab) is selected from the group consisting of huMy9-6, huB4, huDS6, huMov19, and huCD37-3. In other embodiments, the antibody is a humanized CD123 antibody. In certain embodiments, the antibody is AbX. In some embodiments, the AbX antibody comprises the CDR sequences disclosed herein. In some embodiments, the AbX antibody comprises the heavy chain variable region domain sequences and light chain variable region domain sequences disclosed herein.

In some embodiments of the method, the small hydrophobic molecule is trimethylglycine. In further embodiments of the method, the small hydrophobic molecule is proline. In some embodiments of the method, the small hydrophobic molecule is leucine. In certain embodiments of the method, the small hydrophobic molecule is isoleucine. In still further embodiments of the method, two or more small hydrophobic molecules are used in combination in the compositions.

In some embodiments of the method, the composition used in the methods is one of the specific aqueous formulations described above. In certain embodiments of the method, the composition is a reconstituted lyophilized composition derived from one of the aqueous formulations disclosed herein.

In yet another aspect, this disclosure provides a method of formulating a composition, comprising (a) providing an ADC comprising a benzodiazepine in an aqueous solution; and (b) adding to the aqueous solution a small hydrophobic molecule selected from the group consisting of betaines and amino acids with hydrophobic side chains. In some embodiments, the method further comprises adjusting the pH of the aqueous solution to between about 4.0 and about 4.5. In some embodiments of the method, the benzodiazepine is selected from the group consisting of D1, D1(a), D2, D2(a), DGN462, DGN462(a), D3, D3(a), D4, D4(a), D5, D5(a), D6, and D6(a). In certain embodiments of the method, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3(a), Ab-sSPDB-D4, Ab-sSPDB-D4(a), Ab-Cys-D1, Ab-Cys-D1(a), Ab-Ser-D1, Ab-Ser-D1(a), Ab-Cys-DGN462, Ab-Cys-DGN462(a), Ab-Ser-DGN462, Ab-Ser-DGN462(a), Ab-Cys-D5, Ab-Cys-D5(a), Ab-Ser-D6, and Ab-Ser-D6(a). In some embodiments, the antibody is selected from the group consisting of huMy9-6, huB4, huDS6, huMov19, and huCD37-3. In other embodiments, the antibody is a humanized CD123 antibody. In certain embodiments, the antibody is AbX. In some embodiments, the AbX antibody comprises the CDR sequences disclosed herein. In some embodiments, the AbX antibody comprises the heavy chain variable region domain sequences and light chain variable region domain sequences disclosed herein.

In some embodiments of the method, the small hydrophobic molecule is trimethylglycine. In other embodiments of the method, the small hydrophobic molecule is leucine. In some embodiments of the method, the small hydrophobic molecule is isoleucine. In certain embodiments of the method, the small hydrophobic molecule is proline. In still other embodiments of the method, a combination of small hydrophobic molecules are added.

In further embodiments of the method, the addition of a small hydrophobic molecule reduces RSA in the aqueous solution by about 30% to about 40%. In some embodiments, the addition of a small hydrophobic molecule reduces RSA in the aqueous solution by about 40% to about 50%. In certain embodiments, the addition of a small hydrophobic molecule reduces RSA in the aqueous solution by about 50% to about 60%. In further embodiments, the addition of a small hydrophobic molecule reduces RSA in the aqueous solution by about 60% to about 70%. In still further embodiments, the addition of a small hydrophobic molecule reduces RSA in the aqueous solution by about 70% to about 80%. In yet further embodiments, the addition of a small hydrophobic molecule reduces RSA in the aqueous solution by about 80% to about 90%. In some embodiments, the addition of a small hydrophobic molecule reduces RSA in the aqueous solution by about 90% to 100%. In still further embodiments, the addition of a small hydrophobic molecule eliminates RSA in the aqueous solution. In some embodiments, the amount of RSA is measured by multiangle light scattering. In some further embodiments, the amount of RSA is measured by dynamic light scattering.

In some embodiments, the method further comprises lyophilizing the aqueous solution, thereby obtaining a lyophilized composition. In certain embodiments, the method further comprises reconstituting the lyophilized composition, thereby creating a reconstituted lyophilized composition. In further embodiments of the method, the addition of a small hydrophobic molecule reduces RSA in the reconstituted lyophilized composition by about 30% to about 40%. In some embodiments, the addition of a small hydrophobic molecule reduces RSA in the reconstituted lyophilized composition by about 40% to about 50%. In certain embodiments, the addition of a small hydrophobic molecule reduces RSA in the reconstituted lyophilized composition by about 50% to about 60%. In further embodiments, the addition of a small hydrophobic molecule reduces RSA in the reconstituted lyophilized composition by about 60% to about 70%. In still further embodiments, the addition of a small hydrophobic molecule reduces RSA in the reconstituted lyophilized composition by about 60% to about 70%. In yet further embodiments, the addition of a small hydrophobic molecule reduces RSA in the reconstituted lyophilized composition by about 70% to about 80%. In some embodiments, the addition of a small hydrophobic molecule reduces RSA in the reconstituted lyophilized composition by about 80% to about 90%. In certain embodiments, the addition of a small hydrophobic molecule reduces RSA in the reconstituted lyophilized composition by about 90% to about 100%. In some embodiments, the addition of a small hydrophobic molecule eliminates RSA in the reconstituted lyophilized composition.

In still another aspect, this disclosure provides a method of reducing reversible self-association, the method comprising (a) providing an ADC comprising a benzodiazepine in an aqueous solution, wherein the ADC exhibits reversible self association; and (b) adding to the aqueous solution a small hydrophobic molecule selected from the group consisting of betaines and amino acids with hydrophobic side chains, wherein the small hydrophobic molecule reduces reversible self association. In some embodiments, the small hydrophobic molecule is trimethylglycine. In further embodiments, the small hydrophobic molecule is proline. In certain embodiments, the small hydrophobic molecule is leucine. In still further embodiments, the small hydrophobic molecule is isoleucine.

In certain embodiments, the method further comprises detecting reversible self-association. In further embodiments, the method further comprises adjusting the pH of the aqueous solution to between about 4.0 and about 4.5.

In some embodiments of the method, the benzodiazepine is selected from the group consisting of D1, D1(a), D2, D2(a), DGN462, DGN462(a), D3, D3(a), D4, D4(a), D5, D5(a), D6, and D6(a). In certain embodiments of the method, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3 (a), Ab-sSPDB-D4, Ab-sSPDB-D4(a), Ab-Cys-D1, Ab-Cys-D1(a), Ab-Ser-D1, Ab-Ser-D1(a), Ab-Cys-DGN462, Ab-Cys-DGN462(a), Ab-Ser-DGN462, Ab-Ser-DGN462 (a), Ab-Cys-D5, Ab-Cys-D5(a), Ab-Ser-D6, and Ab-Ser-D6 (a). In some embodiments, the antibody is selected from the group consisting of huMy9-6, huB4, huDS6, huMov19, and huCD37-3. In other embodiments, the antibody is a humanized CD123 antibody. In certain embodiments, the antibody is AbX and refers to humanized CD123 antibodies described in U.S. Provisional Application No. 62/186,161, U.S. Patent Application Publication No. US20170029514A1, and PCT Application publication no. WO2017004026. In some embodiments, the AbX antibody comprises the CDR sequences disclosed herein. In some embodiments, the AbX antibody comprises the heavy chain variable region domain sequences and light chain variable region domain sequences disclosed herein.

In some embodiments of the method, the reversible self-association is reduced by about 30% to about 40%. In further embodiments of the method, the reversible self-association is reduced by about 40% to about 50%. In still further embodiments of the method, the reversible self-association is reduced by about 50% to about 60%. In yet further embodiments of the method, the reversible self-association is reduced by about 60% to about 70%. In some embodiments of the method, the reversible self-association is reduced by about 70% to about 80%. In certain embodiments of the method, the reversible self-association is reduced by about 80% to about 90%. In further embodiments of the method, the reversible self-association is reduced by about 90% to about 100%. In certain embodiments of the method, the reversible self-association is eliminated.

In some embodiments, the method further comprises lyophilizing the aqueous solution, thereby creating a lyophilized composition. In further embodiments, the method further comprises reconstituting the lyophilized composition.

It has been discovered that compositions comprising an ADC exhibit reduced reversible self-association when formulated with a buffer (e.g., succinate buffer) at a pH ranging from about 4.0 to about 4.5. Accordingly, yet another aspect of this disclosure is directed to compositions comprising an ADC comprising a benzodiazepine, wherein the ADC exhibits reversible self-association, and a buffer, wherein the composition has a pH ranging from about 4.0 to about 4.5. In some embodiments, the benzodiazepine is selected from the group consisting of D1, D1(a), D2, D2(a), DGN462, DGN462(a), D3, D3(a), D4, D4(a), D5, D5(a), D6, and D6(a). In certain embodiments, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3(a), Ab-sSPDB-D4, Ab-sSPDB-D4(a), Ab-Cys-D1, Ab-Cys-D1(a), Ab-Ser-D1, Ab-Ser-D1 (a), Ab-Cys-DGN462, Ab-Cys-DGN462(a), Ab-Ser-DGN462, Ab-Ser-DGN462(a), Ab-Cys-D5, Ab-Cys-D5(a), Ab-Ser-D6, and Ab-Ser-D6(a). In some embodiments, the antibody is selected from the group consisting of huMy9-6, huB4, huDS6, huMov19, and huCD37-3. In other embodiments, the antibody is a humanized CD123 antibody. In certain embodiments, the antibody is AbX and refers to humanized CD123 antibodies described in U.S. Provisional Application No. 62/186,161, U.S. Patent Application Publication No. US20170029514A1, and PCT Application publication no. WO2017004026. In some embodiments, the AbX antibody comprises the CDR sequences disclosed herein. In some embodiments, the AbX antibody comprises the heavy chain variable region domain sequences and light chain variable region domain sequences disclosed herein.

In some embodiments, the composition further comprises a sugar. In certain embodiments, the sugar is trehalose. In some embodiments, the trehalose is trehalose dihydrate. In other embodiments, the trehalose is trehalose anhydrous. In other embodiments, the sugar is sucrose. In some embodiments, the buffer is succinate. In some embodiments, the composition further comprises sodium bisulfite. In some embodiments, the composition is an aqueous formulation. In other embodiments, the composition is a lyophilized composition. In some embodiments, the composition further comprises a bulking agent. In certain embodiments, the bulking agent is glycine. In other embodiments, the bulking agent is mannitol.

In some embodiments, the aqueous formulation comprises (a) water; (b) huMy9-6-sSPDB DGN462; (c) 10 mM sodium succinate; and (d) 8% trehalose, wherein the formulation has a pH ranging from about 4.0 to about 4.5. In certain embodiments, the aqueous formulation comprises (a) water; (b) AbX D2 or AbX-D2(a); (c) 10 mM sodium succinate; and (d) 8% trehalose, wherein the formulation has a pH ranging from about 4.0 to about 4.5, and optionally includes 2-200 µM sodium bisulfite. In certain embodiments, the aqueous formulation comprises (a) water; (b) AbX-D5 or AbX-D5(a); (c) 10 mM sodium succinate; and (d) 8% trehalose, wherein the formulation has a pH ranging from about 4.0 to about 4.5 and optionally includes 2-200 µM sodium bisulfite. In some embodiments, the aqueous formulation comprises (a) water; (b) 2 mg/mL AbX-D5 or AbX-D5(a); (c) 10 mM sodium succinate; (d) 8% trehalose dihydrate; (e) 50 µM sodium bisulfite; and 0.01% (w/v) polysorbate 20, wherein the formulation has a pH of about 4.2. In some embodiments, the aqueous formulation comprises (a) water; (b) huMov19-sSPDB D1 or D1(a); (c) 10 mM sodium succinate; and (d) 8% trehalose, wherein the formulation has a pH ranging from about 4.0 to about 4.5. In another embodiment, the aqueous formulation comprises (a) water; (b) huMov19-sSPDB D2 or D2(a); (c) 10 mM sodium succinate; and (d) 8% trehalose. In further embodiments, the aqueous formulation comprises (a) water; (b) huMov19-sSPDB D4; (c) 10 mM sodium succinate; and (d) 8% trehalose, wherein the formulation has a pH ranging from about 4.0 to about 4.5. In some embodiments, the composition is a lyophilized composition of any of the aqueous compositions described herein. In some embodiments, the pH of any of the compositions described above is 4.2. In some embodiments, the AbX antibody comprises the CDR sequences disclosed herein. In some embodiments, the AbX antibody comprises the heavy chain variable region domain sequences and light chain variable region domain sequences disclosed herein.

In some embodiments, the composition further comprises a surfactant. In some embodiments, the surfactant is 0.01% polysorbate 20. In some embodiments, the composition further comprises sodium bisulfite. In some embodiments, the composition comprises 2-200 µM sodium bisulfite. In other embodiments, the composition further comprises 5-100 µM sodium bisulfite. In certain embodiments, the composition further comprises about 50 µM sodium bisulfite.

In some embodiments, the pH of the composition is about 4.2. In some embodiments, the aqueous formulation comprises (a) water; (b) 2 mg/mL AbX-D5 or AbX-D5(a); (c) 10 mM sodium succinate; (d) 8% trehalose dihydrate; (e) 50 µM sodium bisulfite; and 0.01% (w/v) polysorbate 20, wherein the formulation has a pH of about 4.2.

Another aspect of this disclosure is directed to a method of reducing reversible self association, comprising (a) providing an ADC comprising a benzodiazepine in an aqueous solution at a first pH, wherein the ADC exhibits reversible self association; and (b) adjusting the pH of the aqueous solution to a second pH ranging from about 4.0 to about 4.5, wherein the adjustment of the pH from the first pH to the second pH reduces reversible self association. In some embodiments, the second pH is about 4.2.

In some embodiments of the disclosed methods, the benzodiazepine is selected from the group consisting of D1, D1(a), D2, D2(a), DGN462, DGN462(a), D3, D3(a), D4, D4(a), D5, D5(a), D6, and D6(a). In some embodiments, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3(a), Ab-sSPDB-D4, Ab-sSPDB-D4(a), Ab-Cys-D1, Ab-Cys-D1(a), Ab-Ser-D1, Ab-Ser-D1(a), Ab-Cys-DGN462, Ab-Cys-DGN462(a), Ab-Ser-DGN462, Ab-Ser-DGN462(a), Ab-Cys-D5, Ab-Cys-D5(a), Ab-Ser-D6, and Ab-Ser-D6(a).

In some embodiments, the reversible self association is reduced by about 70% to about 80%. In further embodiments, the reversible self association is reduced by about 80% to about 90%. In yet further embodiments, the reversible self association is reduced by about 90% to 100%.

In some embodiments, the method further comprises lyophilizing the aqueous solution, thereby creating a lyophilized composition. In still further embodiments, the method also comprises reconstituting the lyophilized composition.

In some embodiments, the ADC comprises an antibody selected from the group consisting of huMy9-6, huB4, huDS6, huMov19, and huCD37-3. In some embodiments, the ADC comprises a humanized CD123 antibody. In some embodiments, the humanized CD123 antibody is AbX. In some embodiments, the AbX antibody comprises the CDR sequences disclosed herein. In some embodiments, the AbX antibody comprises the heavy chain variable region domain sequences and light chain variable region domain sequences disclosed herein.

A further aspect of this disclosure is directed to a composition comprising (a) an ADC comprising a benzodiazepine and (b) trehalose, wherein the composition has a pH ranges from about 4.0 to about 4.5. In some embodiments, the composition further comprises sodium succinate. In some embodiments, the composition further comprises sodium bisulfate. In further embodiments, the composition further comprises a surfactant. In some embodiments, the benzodiazepine is selected from the group consisting of D1, D1(a), D2, D2(a), DGN462, DGN462(a), D3, D3(a), D4, D4(a), D5, D5(a), D6, and D6(a). In further embodiments, the ADC is selected from the group consisting of Ab-sSPDB-D1, Ab-sSPDB-D1(a), Ab-D2, Ab-D2(a), Ab-sSPDB-DGN462, Ab-sSPDB-DGN462(a), Ab-D3, Ab-D3(a), Ab-sSPDB-D4, Ab-sSPDB-D4(a), Ab-Cys-D1, Ab-Cys-D1(a), Ab-Ser-D1, Ab-Ser-D1(a), Ab-Cys-DGN462, Ab-Cys-DGN462(a), Ab-Ser-DGN462, Ab-Ser-DGN462(a), Ab-Cys-D5, Ab-Cys-D5(a), Ab-Ser-D6, and Ab-Ser-D6(a).

DETAILED DESCRIPTION

Figure 1:
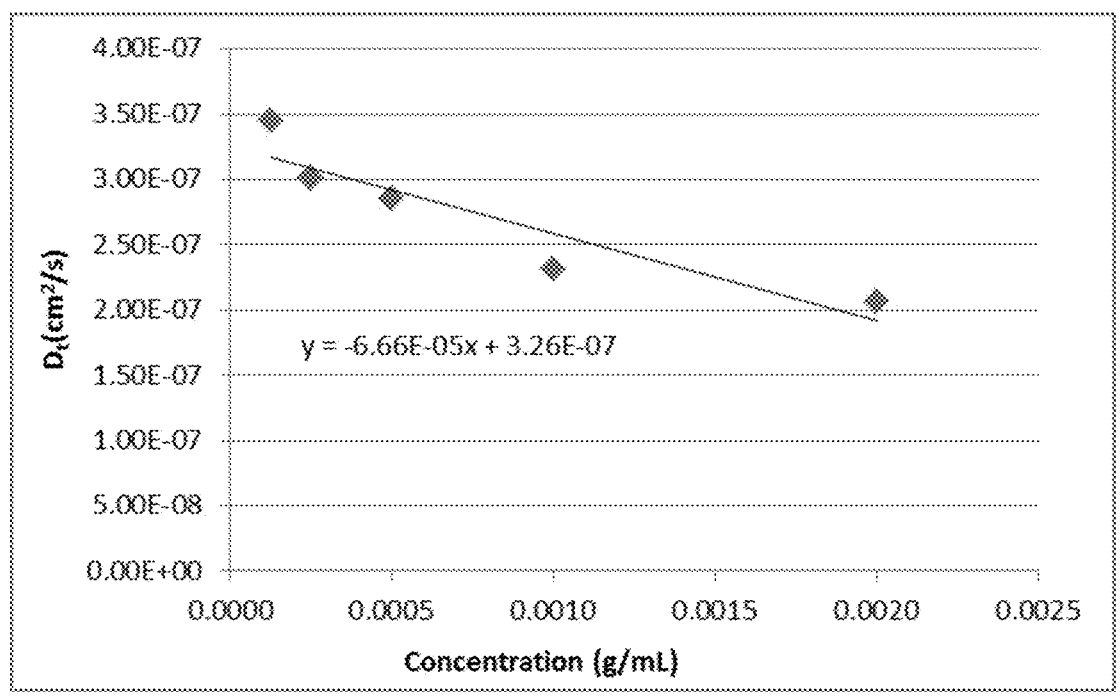
FIG. 1 shows the dynamic light scattering plot of a reversible self-associating system using huM9-6-sSPDB-DGN462 as an example.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the present invention, exemplary suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Definitions

As used herein, the terms "a" or "an" mean one or more unless these terms are otherwise limited in their use.

As used herein, the term "about" means±10% of a stated value.

As used herein, the term "subject" means a human or an animal. Exemplary animals include, but are not limited to, mammals such as mouse, rat, guinea pig, dog, cat, horse, cow, pig, monkey, chimpanzee, baboon, or rhesus monkey.

As used herein, the term "pharmaceutical formulation" refers to a preparation in a form that may be administered to a subject while allowing the biological activity of the active ingredient to be effective.

As used herein, the term "therapeutically effective amount" refers to an amount of a drug that is effective to treat a disease or disorder.

As used herein, "treat", "treating" or "treatment" refers to the reduction, amelioration, or improvement of a disease or disorder, or the reduction, amelioration, or improvement of at least one symptom of a disease or disorder.

As used herein, the term "irreversible aggregate" refers to non-covalent aggregation typically resulting from a hydrophobic interaction due to partial unfolding.

As used herein, the term "chimeric antibody" refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid or reduce the chance of eliciting an immune response in that species (e.g., human). In certain embodiments, a chimeric antibody may include an antibody or antigen-binding fragment thereof comprising at least one human heavy and/or light chain polypeptide, such as, for example, an antibody comprising murine light chain and human heavy chain polypeptides.

As used herein, the term "antigen-binding fragment" of an antibody refers to one or more fragments of an antibody that retain the ability to specifically bind to an antigen.

As used herein, "polyclonal" antibodies refer to heterogeneous populations of antibody, typically contained in the sera of immunized animals.

As used herein, "monoclonal" antibodies refer to homogenous populations of antibody molecules that are specific to a particular antigen.

As used herein, the terms "linker," "linking group," or "linking moiety" refer to a moiety that connects two groups, such as an antibody and a cytotoxic compound, together.

As used herein, the terms "cancer" and "cancerous" refer to or describe the physiological condition in mammals in which a population of cells are characterized by unregulated cell growth. Cancer can include a hematological cancer or a solid tumor.

Aggregates and Reversible Self-Association

Development of commercially viable and clinically useful ADC compositions is complicated by the unpredictable behaviors of different antibodies and ADCs during formulation. The ability of antibodies and ADCs to aggregate and reversibly self-associate can lead to many undesirable effects commercially and clinically. Aggregation and reversible self-association can lead to reduced potency, decreased stability, increased toxicity, increased viscosity, discoloration of solution, and other undesirable effects. In some circumstances, aggregates can trigger an immune system response, a potential safety concern in patients.

Covalent aggregates occur through the formation of a chemical bond between at least two monomers. For example, covalent aggregates can result from disulfide bonds formed between unpaired cysteines on a monomer, or as a result of intermolecular disulfide scrambling, or through thioether linking.

In certain instances, aggregation is irreversible. The irreversible aggregation of immunoglobulins leads to decreased activity or functionality of the immunoglobulins in formulations. Irreversible aggregates can be inhibited by agents such as urea, guanidine, or sodium dodecyl sulfate ("SDS"), but not through reducing the concentration of the antibody.

Reversible self-association ("RSA") occurs as a result of an ADC's ability to form oligomeric species through weak, non-covalent intermolecular interactions. The amount of these interactions for any given ADC in solution depends on a variety of factors, including the antibody itself (e.g., primary and secondary structures) and solution characteristics such as pH, as well as ADC concentration. Furthermore, it has been discovered that the amount and extent of the self-association varies by ADC depending on the characteristics of the cytotoxic compound and the antibody. Cytotoxic compounds that are hydrophobic, insoluble, and/or comprise multiple aromatic rings can increase RSA. Therefore, more hydrophobic ADCs have an increased tendency to reversibly self-associate in solution. The ADCs self-associate and attain equilibrium in solution between monomers and in higher ordered oligomeric species.

ADC reversible self-association has numerous detrimental effects in formulations. RSA can create problems for manufacturing, stability, delivery, and safety of the ADC in a therapeutic context. From a delivery perspective, RSA can increase the viscosity of a solution, which can impede the plunger of a pre-filled syringe. From a stability and safety perspective, RSA can reduce potency (because the oligomeric species do not function therapeutically) and increase the possibility of triggering an immune response.

Researchers have several methods at their disposal to assess the amount of ADC monomer in solution. For example, the amount of ADC monomer in solution can be measured by size exclusion chromatography (both SEC and SEC-MS) and sedimentation velocity (SV). Under SEC analysis, ADC aggregates elute more quickly than ADC monomers that are smaller and able to travel deeper into the pores of the SEC packing material. SEC can provide good separation between aggregates and monomers, thereby providing a good estimation of the amount of monomer in the solution.

As explained in greater detail in the Examples below, SV analyzes the behavior of the ADC in solution by applying angular acceleration to the solution (generally through centrifugation) to cause the ADCs to sediment. Generally, larger particles, e.g., ADC aggregates or reversibly self-associated oligomers, sediment more quickly. Therefore, SV can be used to assess the amount of ADC monomer in solution because the aggregates and oligomers sediment more quickly than the monomers.

In some instances, SEC or SEC-MS and SV may give different monomer percentages for the same antibody. Such discrepancies can indicate the presence of reversibly self-associating monomers. Moreover, changes in concentration and solution characteristics typically reduce RSA, but may not affect the amount of either covalent or irreversible aggregates present.

Multiangle Light Scattering ("MALS") can be used to determine the amount of reversibly associated oligomers in a given solution based on how the monomers and the oligomers of different order scatter light. As the concentration of an antibody in solution increases, MALS typically detects the increase of a species of higher molecular weight, e.g., an oligomer, than the monomer. This increase indicates an increase in RSA.

Dynamic Light Scattering ("DLS") can also be used to determine the existence and extent of RSA in a solution. DLS involves measuring the time-dependent change in intensity of light scattered by a species in solution. Typically, DLS-measuring instruments yield the hydrodynamic diameter of a particle. As the concentration of an antibody in solution increases, a DLS-measuring instrument will detect an increased presence of species having greater hydrodynamic diameters, e.g., oligomers. This increase indicates an increase in RSA. DLS-measuring instruments can also be used to determine the diffusion coefficients of the species in solution. Diffusion coefficients decrease with increased antibody concentration, indicating the existence of RSA.

ADCs

This disclosure is directed to ADCs, compositions comprising ADCs, methods of treating, methods of formulating ADC compositions, and methods of reducing RSA in ADCs. ADCs comprise an antibody, or an antibody fragment, conjugated to a cytotoxic compound. In some embodiments, the cytotoxic compound is conjugated to an antibody via a linker. In other embodiments, the cytotoxic compound is linked directly to the antibody. The types of antibodies, linkers, and cytotoxic compounds encompassed by this disclosure are described below.

Antibodies

Disclosed herein are compositions that comprise antibodies and antigen-binding fragments thereof. Antibodies are large glycoproteins that can exist as soluble and membrane-bound forms and comprise five natural isotypes—IgA, IgD, IgE, IgG, and IgM, based on the identity of their heavy-chain constant domains referred to as alpha, delta, epsilon, gamma, and mu, respectively. The different classes of immunoglobulins have different and well-known subunit structures and three-dimensional configurations. As one of ordinary skill in the art will recognize, the disclosed compositions can comprise polyclonal antibodies and monoclonal antibodies. In particular embodiments, the antibodies comprise antibodies such as multispecific antibodies such as bispecific antibodies, chimeric antibodies, humanized antibodies, and human antibodies. The compositions can also comprise antibodies that have one or more conservative or non-conservative amino acid substitutions. Furthermore, the compositions can comprise modified glycosylation at one or more amino acid residues. Such modified antibodies or binding fragments fall within the scope of the compositions disclosed herein so long as the modified antibodies exhibit the desired biological activity.

As used herein, a "humanized" antibody is one in which the complementarity-determining regions (CDRs) of a mouse monoclonal antibody, which form the antigen binding loops of the antibody, are grafted onto the framework of a human antibody molecule or where the variable domains of the framework of a murine antibody have been resurfaced (i.e., the exposed residues are replaced with the residues that are present in the corresponding positions of human antibodies). See, e.g., Roguska et. al, Protein Engineering, Vol 9. No. 10, pp. 895-904, 1996.

Exemplary antibodies include humanized monoclonal antibodies, examples of which include, huMy9-6, huB4, huDS6, huMov19, and huCD37-3. Exemplary antibodies also include humanized CD123 antibodies, exemplary sequences of which are described in U.S. application publication no. US20170029514A1 and PCT application publication no. WO2017004026 and are referred to herein as "AbX".

Specific examples of humanized CD123 antibodies (AbX) described in U.S. application publication no. US20170029514A1 and PCT application publication no. WO2017004026 and included in the AbX embodiments described herein are:

Humanized CD123 antibodies that include the following heavy chain variable region CDR amino acid sequences:

$V_H$ CDR1:
SSIMH
(SEQ ID NO: 1)

$V_H$ CDR2:
YIKPYNDGTKYNEKFKG
(SEQ ID NO: 2)

$V_H$ CDR3:
EGGNDYYDTMDY
(SEQ ID NO: 3)

Humanized CD123 antibodies that include the following light chain variable region CDR amino acid sequences:

$V_L$ CDR1:
RASQDINSYLS
(SEQ ID NO: 4)

$V_L$ CDR2:
RVNRLVD
(SEQ ID NO: 5)

V$_L$ CDR3:

(SEQ ID NO: 6)
LQYDAFPYT

Humanized anti-CD123 antibodies that include the following heavy chain variable region amino acid sequences:

AbX$_1$:

(SEQ ID NO: 7)
Q(F/V)QLVQSGAEVKKPGASVKVSCKASGYIFTSSIMHWVRQAPGQGLE
WIGYIKPYNDGTKYNEKFKGRATLTSDRSTSTAYMELSSLRSEDTAVYYC
AREGGNDYYDTMDYWGQGTLVTVSS

AbX$_2$:

(SEQ ID NO: 8)
QVQLVQSGAEVKKPGASVKVSCKASGYGFTSSIMHWVRQAPGQGLEWMGY
IKPYNDGTKYNEKFKGRVTMTRDTSTSTVYMELSSLRSEDTAVYYCAREG
GNDYYDTMDYWGQGTLVTVSS

Humanized anti-CD123 antibodies that include the following light chain variable region amino acid sequences:

AbX$_1$:

(SEQ ID NO: 9)
DIQMTQSPSSLSASVGDRVTITCRASQDINSYLSWFQQKPGKAPKTLIYR
VNRLVDGVPSRFSGSGSGNDYTLTISSLQPEDFATYYCLQYDAFPYTFGQ
GTKVEIKR

AbX$_2$:

(SEQ ID NO: 10)
DIQMTQSPSSLSASVGDRVTITCRASQDINSYLAWFQQKPGKAPKSLIYR
VNRLVSGVPSRFSGSGSGTDFTLTISSLQPEDFATYYCLQYDAFPYTFGQ
GTKVEIKR

In other specific embodiments, the anti-CD123 antibody or antigen-binding fragment thereof comprises an engineered Cys residue (e.g., C442); an immunoglobulin heavy chain variable domain at least about 90%, 95%, 99% or 100% identical to QXQLVQSGAEVKKPGASVKVSCKASGYIFTSSIMHWVRQAPGQGLEWIGYIKPY NDGTKYNEKFKGRATLTSDRSTSTAYMELSSLRSEDTAVYYCAREGGNDYYDT MDYWGQGTLVTVSS (SEQ ID NO: 7); and an immunoglobulin light chain variable region having the amino acid sequence at least about 90%, 95%, 99% or 100% identical to DIQMTQSPSSLSASVGDRVTITCRASQDIN-SYLSWFQQKPGKAPKTLIYRVNRLV DGVPSRFSGSGSGNDYTLTISSLQPEDFATYY-CLQYDAFPYTFGQGTKVEIKR (SEQ ID NO: 9). In certain embodiments, Xaa, the second residue from the N-terminus of SEQ ID NO: 7, is Phe. In other embodiments, Xaa is Val.

In other specific embodiments, the anti-CD123 antibody or antigen-binding fragment thereof comprises an engineered Cys residue (e.g., C442); an immunoglobulin heavy chain variable domain at least about 90%, 95%, 99% or 100% identical to QVQLVQSGAEVKKPGASVKVSCK-ASGYGFTSSIMHWVRQAPGQGLEWMGYIKP YNDGTKYNEKFKGRVTMTRDTST-STVYMELSSLRSEDTAVYYCAREGGNDYYD TMDYWGQGTLVTVSS (SEQ ID NO: 8); and an immunoglobulin light chain variable region having the amino acid sequence at least about 90%, 95%, 99% or 100% identical to (SEQ ID NO: 10)
DIQMTQSPSSLSASVGDRVTITCRASQDINSYLAWFQQKPGKAPKSLIYR
VNRLVSGVPSRFSGSGSGTDFTLTISSLQPEDFATYYCLQYDAFPYTFGQ
GTKVEIKR.

Humanized anti-CD123 antibodies that include the following heavy chain amino acid sequences:

AbX$_1$:

(SEQ ID NO: 11)
Q(F/V)QLVQSGAEVKKPGASVKVSCKASGYIFTSSIMHWVRQAPGQGLE

WIGYIKPYNDGTKYNEKFKGRATLTSDRSTSTAYMELSSLRSEDTAVYYC

AREGGNDYYDTMDYWGQGTLVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPG

AbX$_{1C}$:

(SEQ ID NO: 12)
Q(F/V)QLVQSGAEVKKPGASVKVSCKASGYIFTSSIMHWVRQAPGQGLE

WIGYIKPYNDGTKYNEKFKGRATLTSDRSTSTAYMELSSLRSEDTAVYYC

AREGGNDYYDTMDYWGQGTLVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLC

LSPG

AbX$_2$:

(SEQ ID NO: 13)
QVQLVQSGAEVKKPGASVKVSCKASGYGFTSSIMHWVRQAPGQGLEWMGY

IKPYNDGTKYNEKFKGRVTMTRDTSTSTVYMELSSLRSEDTAVYYCAREG

GNDYYDTMDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

Humanized anti-CD123 antibodies that include the following light chain amino acid sequences:

AbX₁:
(SEQ ID NO: 14)
DIQMTQSPSSLSASVGDRVTITCRASQDINSYLSWFQQKPGKAPKTLIYR

VNRLVDGVPSRFSGSGSGNDYTLTISSLQPEDFATYYCLQYDAFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

AbX₂:
(SEQ ID NO: 15)
DIQMTQSPSSLSASVGDRVTITCRASQDINSYLAWFQQKPGKAPKSLIYR

VNRLVSGVPSRFSGSGSGTDFTLTISSLQPEDFATYYCLQYDAFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In other specific embodiments, the anti-CD123 antibody or antigen-binding fragment thereof comprises an engineered Lys residue; an immunoglobulin heavy chain variable domain at least about 90%, 95%, 99% or 100% identical to Q(F/V)QLVQSGAEVKKPGASVKVSCKASGYIFTSSIMHWVRQAPGQGLEWIGYIK PYNDGTKYNEKFKGRATLTSDRSTSTAYMELSSLRSEDTAVYYCAREGGNDYYDTMDYWGQGTLVTVSSASTKGPSVFPLAPSSKSTSGGTAALGCLVKDYFPEPVT VSWNSGALTSGVHTFPAVLQSSGLYS-LSSVVTVPSSSLGTQTYICNVNHKPSNTK VDKKVEPKSCDKTHTCPPCPA-PELLGGPSVFLFPPKPKDTLMISRTPEVTCVVVD VSHEDPEVKFNWYVDGVEVHNAKTKPREEQYN-STYRVVSVLTVLHQDWLNGK EYKCKVSNKALPA-PIEKTISKAKGQPREPQVYTLPPSRDELTKNQVSLT-CLVKGF YPSDIAVEWESNGQPENNYKTTPPVLDSDGSFFLY-SKLTVDKSRWQQGNVFSCS VMHEALHN-HYTQKSLSLSPG (SEQ ID NO: 11); and an immunoglobulin light chain variable region having the amino acid sequence at least about 90%, 95%, 99% or 100% identical to DIQMTQSPSSLSASVGDRVTITCRASQDIN-SYLSWFQQKPGKAPKTLIYRVNRLV DGVPSRFSGSGSGNDYTLTISSLQPEDFATYY-CLQYDAFPYTFGQGTKVEIKRTV AAPSVFIFPPSD-EQLKSGTASVVCLLNNFYPREAKVQWKVD-NALQSGNSQESVT EQDSKDSTYSLSSTLTLSKADYEKHKVYACE-VTHQGLSSPVTKSFNRGEC (SEQ ID NO: 14). In certain embodiments, Xaa, the second residue from the N-terminus of SEQ ID NO: 11, is Phe. In other embodiments, Xaa is Val.

In other specific embodiments, the anti-CD123 antibody or antigen-binding fragment thereof comprises an immunoglobulin heavy chain variable domain at least about 90%, 95%, 99% or 100% identical to Q(F/V)QLVQSGAEVKKPGASVKVSCKASGYIFTSSIMHWVRQAPGQGLEWIGYIK PYNDGTKYNEKFKGRATLTSDRSTSTAYMELSSLRSEDTAVYYCAREGGNDYYDTMDYWGQGTLVTVSSASTKGPSVFPLAPSSKSTSGGTAALGCLVKDYFPEPVT VSWNSGALTSGVHTFPAVLQSSGLYS-LSSVVTVPSSSLGTQTYICNVNHKPSNTK VDKKVEPKSCDKTHTCPPCPA-PELLGGPSVFLFPPKPKDTLMISRTPEVTCVVVD VSHEDPEVKFNWYVDGVEVHNAKTKPREEQYN-STYRVVSVLTVLHQDWLNGK EYKCKVSNKALPA-PIEKTISKAKGQPREPQVYTLPPSRDELTKNQVSLT-CLVKGF YPSDIAVEWESNGQPENNYKTTPPVLDSDGSFFLY-SKLTVDKSRWQQGNVFSCS VMHEALHN-HYTQKSLCLSPG (SEQ ID NO: 12); and an immunoglobulin light chain variable region having the amino acid sequence at least about 90%, 95%, 99% or 100% identical to DIQMTQSPSSLSASVGDRVTITCRASQDIN-SYLSWFQQKPGKAPKTLIYRVNRLV DGVPSRFSGSGSGNDYTLTISSLQPEDFATYY-CLQYDAFPYTFGQGTKVEIKRTV AAPSVFIFPPSD-EQLKSGTASVVCLLNNFYPREAKVQWKVD-NALQSGNSQESVT EQDSKDSTYSLSSTLTLSKADYEKHKVYACE-VTHQGLSSPVTKSFNRGEC (SEQ ID NO: 14). In certain embodiments, Xaa, the second residue from the N-terminus of SEQ ID NO: 12, is Phe. In other embodiments, Xaa is Val.

In other specific embodiments, the anti-CD123 antibody or antigen-binding fragment thereof comprises an immunoglobulin heavy chain variable domain at least about 90%, 95%, 99% or 100% identical to QVQLVQSGAEVKKP-GASVKVSCKASGYGFTSSIMHWVRQAPGQ-GLEWMGYIKP YNDGTKYNEKFKGRVTMTRDTST-STVYMELSSLRSEDTAVYYCAREGGNDYYD TMDYWGQGTLVTVSSASTKGPSVFPLAPSSKST-SGGTAALGCLVKDYFPEPVTV SWNSGALT-SGVHTFPAVLQSSGLYS-LSSVVTVPSSSLGTQTYICNVNHKPSNTKV DKKVEPKSCDKTHTCPPCPA-PELLGGPSVFLFPPKPKDTLMISRTPEVTCVVVDVS HEDPEVKFNWYVDGVEVHNAKTKPREEQYN-STYRVVSVLTVLHQDWLNGKEY KCKVSNKALPA-PIEKTISKAKGQPREPQVYTLPPSRDELTKNQVSLT-CLVKGFYPS DIAVEWESNGQPENNYKTTPPVLDSDGSFFLYSK-LTVDKSRWQQGNVFSCSVMH EALHNHYTQKSLSL-SPG (SEQ ID NO: 13); and an immunoglobulin light chain variable region having the amino acid sequence at least about 90%, 95%, 99% or 100% identical to (SEQ ID NO: 15)
DIQMTQSPSSLSASVGDRVTITCRASQDINSYLAWFQQKPGKAPKSLIYR

VNRLVSGVPSRFSGSGSGTDFTLTISSLQPEDFATYYCLQYDAFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

Exemplary sequences for huDS6 are described in U.S. Pat. No. 7,834,155 and International Pat. Appl. Publication Nos.: WO2005/009369 and WO2007/024222, which are incorporated herein by reference in their entireties. Detailed sequences for huMov19 are described in U.S. Pat. Nos. 8,557,966 and 8,709,432 and International Pat. Appl. Publication Nos.: WO2011/106528, which are incorporated herein by reference in their entireties. Exemplary sequences for the huMy9-6 heavy chain variable region portion are described in U.S. Patent Publication No. 20060177455, which is incorporated herein by reference in its entirety. Exemplary sequences for the huMy9-6 light chain variable region portion are known in the art and described in U.S. Pat. Nos. 7,557,189, 7,342,110, 8,119,787 and 8,337,855, which are incorporated herein by reference in their entireties. Exemplary sequences for huCD37-3 are described in U.S. Pat. No. 8,765,917 and International Pat. Appl. Publication No. WO2011/112978, which are incorporated herein by reference in their entireties. Exemplary sequences for huB4 is described in International Pat. Appl. Publication No. WO2012/156455, which is incorporated herein by reference in its entirety.

Additional exemplary antibodies include antibodies that target specific antigens. Examples include antibodies that target CD33, CD19, CD37, CA6, or FOLR1. Further, antibodies that target CD123 are also included herein.

Generally, the term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al, Nature 321:522-525, 1986; Riechmann et al, Nature 332:323-327, 1988; Verhoeyen et al, Science 239:1534-1536, 1988).

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5):489-498; Studnicka G. M. et al., 1994, Protein Engineering 7(6):805-814; Roguska M. A. et al., 1994, PNAS 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and International Pat. Appl. Publication Nos.: WO 98/46645, WO 98/50433, WO 98/24893, WO 98/16654, WO 96/34096, WO 96/33735, and WO 91/10741 (said references incorporated by reference in their entireties).

In some instances, the $F_v$ framework region (FR) residues of a human immunoglobulin are replaced with the corresponding residues in an antibody from a non-human species that has the desired specificity, affinity, and capability. The humanized antibody can be further modified by the substitution of additional residues either in the $F_v$ framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641, Roguska et al, Proc. Natl. Acad. Sci. USA 91(3):969-973, 1994; and Roguska et al, Protein Eng. 9(10):895-904, 1996 (all incorporated herein by reference). In some embodiments, a "humanized antibody" is a resurfaced antibody. In some embodiments, a "humanized antibody" is a CDR-grafted antibody.

In addition, the antibody can be a chimeric antibody.

The disclosed compositions can comprise antigen-binding fragments such as antibody fragments (such as Fab, Fab', F(ab)2, and Fv fragments) or single chain Fv (scFv) mutants. In other embodiments, the binding fragments are attached to a separate protein, peptide, or oligopeptide to form a fusion protein. In certain embodiments, the fusion protein comprises an antigen-determination portion of an antibody fused to a one or more peptides, oligopeptides, or polypeptides.

One of ordinary skill in the art will appreciate that the selection of an appropriate antibody will depend upon the cell population to be targeted. In this regard, the type and number of cell surface molecules (i.e., antigens) that are selectively expressed in a particular cell population (typically a diseased cell population) will inform the selection of an appropriate antibody for use in the disclosed compositions. Cell surface expression profiles are known for a wide variety of cell types, including tumor cell types, or, if unknown, can be determined using routine molecular biology and histochemistry techniques.

As noted herein, the antibodies can be polyclonal or monoclonal. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, Eur. J. Immunol., 5, 511-519 (1976), Harlow and Lane (eds.), Antibodies: A Laboratory Manual, CSH Press (1988), and C. A. Janeway et al. (eds.), Immunobiology, 5th Ed., Garland Publishing, New York, N.Y. (2001)). In brief, the hybridoma method of producing monoclonal antibodies typically involves injecting any suitable animal, typically a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, J. Immunol. Methods, 74(2), 361-67 (1984), and Roder et al., Methods Enzymol., 121, 140-67 (1986)), or bacteriophage vector expression systems (see, e.g., Huse et al., Science, 246, 1275-81 (1989)). To prepare monoclonal antibody fragments, recombinant methods typically are employed.

The monoclonal antibody can be isolated from or produced in any suitable animal. In some embodiments, the antibody is produced in a mammal. In some embodiments, the mammal is a mouse. In some embodiments, the mammal is a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

Although effective for human therapeutic use, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of an ADC. To circumvent these complications, a monoclonal antibody preferably is not recognized as "foreign" by the human immune system. To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example U.S. Pat. Nos. 5,545,806 and 5,569,825, and Janeway et al., supra. In some embodiments, the antibody is a humanized antibody. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641, Pedersen et al., J. Mol. Biol., 235, 959-973 (1994), Roguska et al., Proc. Natl. Acad. Sci. USA 91(3):969-973, 1994; and Roguska et al, Protein Eng. 9(10):895-904, 1996.

Antibody fragments that have at least one antigen-binding site, and thus recognize and bind to at least one antigen or receptor present on the surface of a target cell, also are within the scope of this disclosure. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab')2 fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments of the present disclosure, however, are not limited to these exemplary types of antibody fragments. Any suitable antibody fragment that recognizes and binds to a desired cell surface receptor or antigen can be employed. Antibody-antigen binding can be assayed using any suitable method known in the art, such as, for example, radioimmunoassay (MA), ELISA, Western blot, immunoprecipitation, and competitive inhibition assays (see, e.g., Janeway et al., supra, and U.S. Patent Application Publication No. 2002/0197266 A1).

Linkers

Aspects of the compositions disclosed herein comprise antibodies and antigen-binding fragments thereof attached to a linker. Any suitable linker can be used with the ADCs of the present disclosure as long as the linker does not prevent the antibody from binding to its target or eliminate a cytotoxic compound's cytotoxicity. Typically, a linker is substantially inert under conditions for linking two groups. In some embodiments, a linker moiety comprises two reactive groups, such that one reactive group can be first reacted with the cytotoxic compound to provide a compound bearing the linker moiety and a second reactive group, which can then react with an antibody. Alternatively, one reactive group of the linker moiety can be first reacted with an antibody to provide an antibody and a linker moiety and a second reactive group, which can then react with a cytotoxic compound.

Exemplary linkers include, but are not limited to, disulfide linkers, thioether linkers, amide bonded linkers, peptidase-labile linkers, acid-labile linkers, and esterase-labile linkers. In some embodiments, the linker is cleavable. Exemplary cleavable linkers include, but are not limited to, N-succinimidyl 3-(2-pyridyldithio) propionate (SPDP), N-succinimidyl 4-(2-pyridyldithio)butanoate (SPDB), N-succinimidyl 4-(2-pyridyldithio)2-sulfobutanoate (sulfo-SPDB), N-succinimidyl 4-(2-pyridyldithio)pentanoate (SPP), or N-succinimidyl 4-methyl-4-[2-(5-nitro-pyridyl)-dithio]pentanoate (SMNP). In some embodiments, the linker is non-cleavable. Exemplary non-cleavable linkers include, but are not limited to, 2-iminothiolane, acetylsuccinic anhydride, and succinimidyl 4-(maleimidomethyl)cyclohexanecarboxylate (SMCC). Other exemplary linkers, such as CX1-1 (as described in U.S. Pat. Publication No. US20120253021, which is incorporated herein by reference) and acetylsuccinic anhydride, can be used as cleavable or non-cleavable linkers.

In some embodiments, the linking moiety contains a chemical bond that allows for the release of the cytotoxic compound at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913, 748; 7,276,497; 7,276,499; 7,368,565; 7,388,026 and 7,414, 073). Other suitable linkers include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference.

Cytotoxic Compounds

Aspects of this disclosure are directed to several cytotoxic compounds. These cytotoxic compounds can induce cytotoxicity in cells. When coupled to any of the above-described antibodies to form the ADCs of this disclosure, these cytotoxic compounds can be delivered directly to targeted cells. As a result of normal pharmacologic clearance mechanisms, an antibody employed in an ADC contacts and binds to target cells only in limited amounts. Therefore, the cytotoxic agent employed in the conjugate must be highly cytotoxic such that cell killing sufficient to elicit a therapeutic effect occurs.

The cytotoxic compounds of this disclosure comprise benzodiazepines. In some embodiments, the cytotoxic compound is a pyrrolobenzodiazepine. In some embodiments, the cytotoxic compound is a indolinobenzodiazepine. In some embodiments, the cytotoxic compound is a compound in Table 1. DGN462 is described, for example, in U.S. Pat. No. 8,765,740, which is incorporated herein by reference in its entirety. Compound D3 is described, for example, in U.S. Pat. Nos. 8,426,402, 8,809,320 and 8,802,667, which are incorporated herein by reference in their entirety. Compounds D1, D2, and D4 are described, for example, in U.S. Application Publication Numbers US20160106863A1 and US20160082114A1, which are both incorporated herein by reference, and "Antibody-Drug Conjugates (ADCs) of Indolino-Benzodiazepine DNA-Alkylating Agents", 2015 AACR, Abstract number 652, which is incorporated herein by reference.

TABLE 1

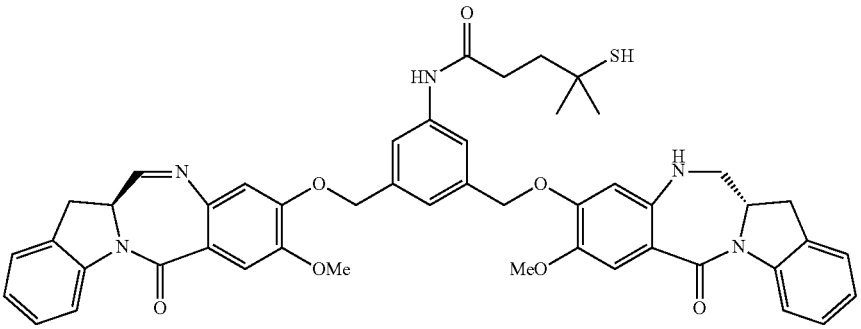 [SMILES: COc1cc2c(cc1OCc1cc(COc3cc4c(cc3OC)C(=O)N3c5ccccc5C[C@H]3CN4)cc(NC(=O)CCC(C)(C)S)c1)N=C[C@@H]1Cc3ccccc3N1C2=O]

TABLE 1-continued
| Compound Name | Compound |
|---|---|
| D2(a) | 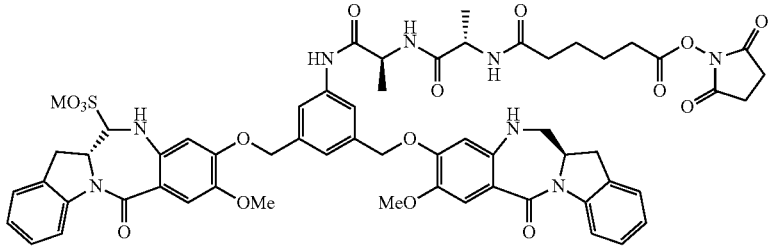 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)ON3C(=O)CCC3=O)c1)N=C[C@@H]1Cc3ccccc3N1C2=O]<br>M = Na+, K+, H or any pharmaceutically acceptable cation |
| DGN462 | 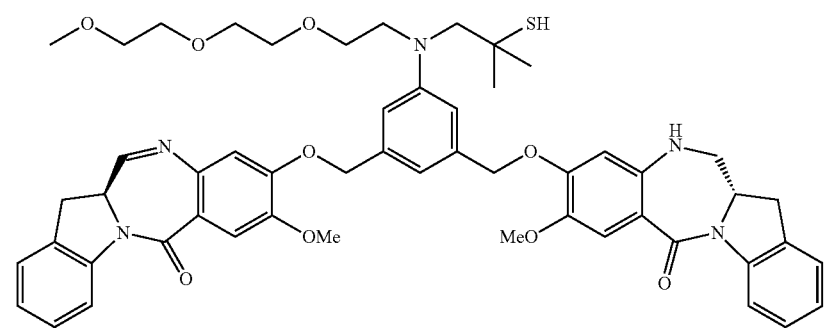 [SMILES: COCCOCCOCCN(CC(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| DGN462(a) | 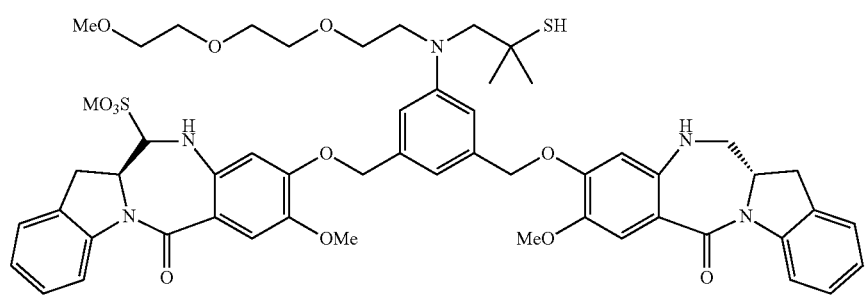<br>M = Na+, K+, H or any pharmaceutically acceptable cation |
| D3 | 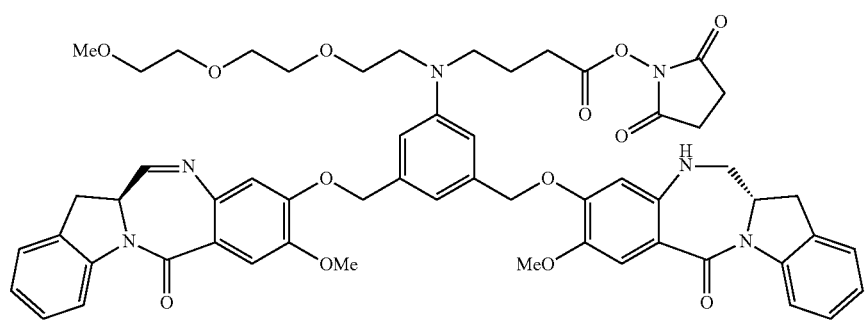 [SMILES: COCCOCCOCCN(CCCC(=O)ON1C(=O)CCC1=O)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |

TABLE 1-continued
| Compound Name | Compound |
| --- | --- |
| D3(a) | 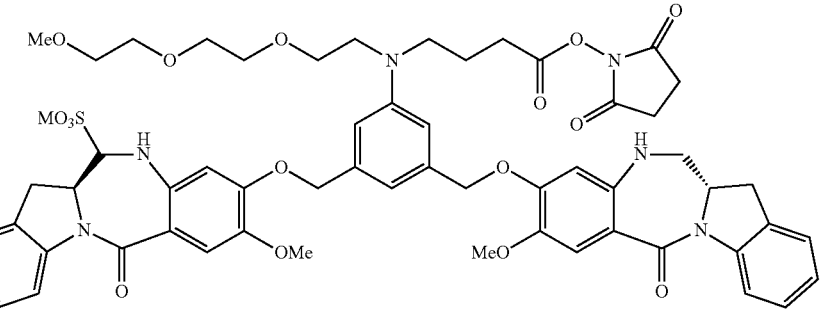 M = Na+, K+, H or any pharmaceutically acceptable cation |
| D4 | 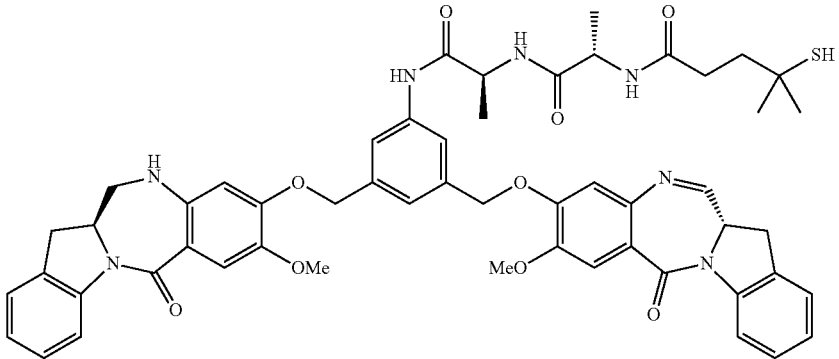 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCC(C)(C)S)c1)N=C[C@@H]1Cc3ccccc3N1C2=O] |
| D4(a) | 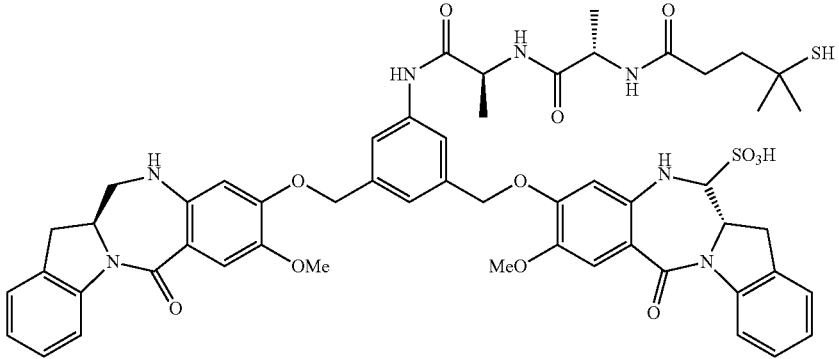 |
| D5 | 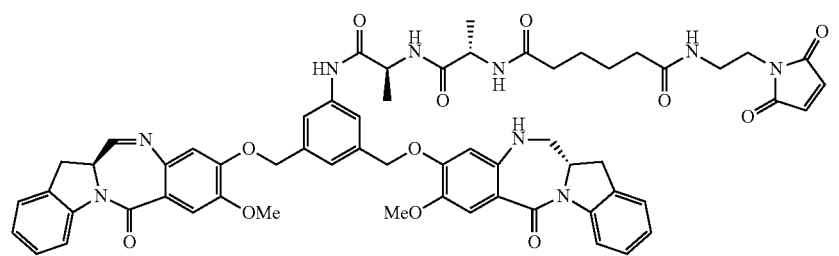 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O] |

TABLE 1-continued

| Compound Name | Compound |
|---|---|
| D5(a) | (structure) M = Na+, K+, H or any pharmaceutically acceptable cation |
| D6 | (structure) |
| D6(a) | (structure) M = Na+, K+, H or any pharmaceutically acceptable cation |

The benzodiazepines, including the compounds in Table 1, are linked to antibodies and antigen-binding fragments thereof with the linkers described herein. In some embodiments of the ADCs, the benzodiazepines may be Cys-linked. In other embodiments, the benzodiazepines may be Ser-linked.

This disclosure is also directed to variations of the compounds in Table 1, such as modification of a compound in Table 1 by sulfonation. Other variations of the compounds in Table 1 are readily apparent to those of ordinary skill in the art. Such variations are encompassed by this disclosure.

Increased RSA in ADCs

ADCs comprising benzodiazepines are shown herein to exhibit increased RSA. It is believed that the increased RSA results from the increased hydrophobic interactions from the benzodiazepines resulting in additional reversible intermolecular interactions. As demonstrated below in the Examples, an increase in the drug load (the "DAR" or drug-to-antibody ratio) results in increased RSA. Compositions with higher DARs have higher amounts of benzodiazepines per antibody. The benzodiazepines are hydrophobic and insoluble and comprise multiple aromatic rings. Thus, it is believed the benzodiazepines interact with other components in an ADC. These additional reversible intermolecular interactions result in increased RSA for the ADCs disclosed herein. Therefore, the amount of RSA increases as the drug load increases. As a result, it is even more difficult to develop pharmaceutical formulations for ADCs comprising hydrophobic molecules (e.g., benzodiazepines or indolinobenzodiazepines) of this disclosure.

Reduced RSA Compositions

It has been surprisingly discovered that certain small hydrophobic molecules inhibit or reduce RSA in compositions comprising the ADCs of this disclosure. These small molecules fall into two classes: (1) amino acids with hydrophobic side chains, including proline, alanine, leucine, isoleucine, methionine, phenylalanine, tryptophan, tyrosine, and valine; and (2) betaines, small neutral molecules with a positively charged cationic functional group and a negatively charged functional group. The cationic functional group and negatively charged functional group need not be adjacent. The cationic functional groups include onium ions such as quaternary ammonium and quaternary phosphonium. The negatively charged functional groups include carboxylate, sulfite, and phosphite. An exemplary betaine is trimethylglycine. Historically, the term betaine referred to trimethylglycine. Therefore, depending on the context as used herein, the term "betaine" can refer to betaines generally or to trimethylglycine specifically.

One aspect of this disclosure is directed to a composition comprising: (a) an ADC comprising a benzodiazepine; and (b) a small hydrophobic molecule selected from the group consisting of betaines and or amino acids with hydrophobic side chains. In some embodiments, the small hydrophobic molecule is an amino acid with a hydrophobic side chain. In some embodiments, the small hydrophobic molecule is a betaine. In some embodiments, the small hydrophobic molecule is trimethlyglycine. In some embodiments, the antibody is selected from the group consisting of huMy9-6, huB4, huDS6, huMov19, and huCD37-3. In other embodiments, the antibody is a humanized CD123 antibody. In certain embodiments, the antibody is AbX. In some embodiments, the benzodiazepine is an indolinobenzodiazepine. In some embodiments, the benzodiazepine is a compound in Table 1. In some embodiments, the ADC is an ADC in Table 2.

TABLE 2

| Conjugate Name | Conjugate Structure |
|---|---|
| Ab-sSPDB-D1 | |
| Ab-sSPDB-D1(a) | |
| Ab-D2 | |

TABLE 2-continued
| Conjugate Name | Conjugate Structure |
|---|---|
| Ab-D2(a) | |
| Ab-sSPDB-DGN462 | |
| Ab-sSPDB-DGN462(a) | |
| Ab-D3 | |
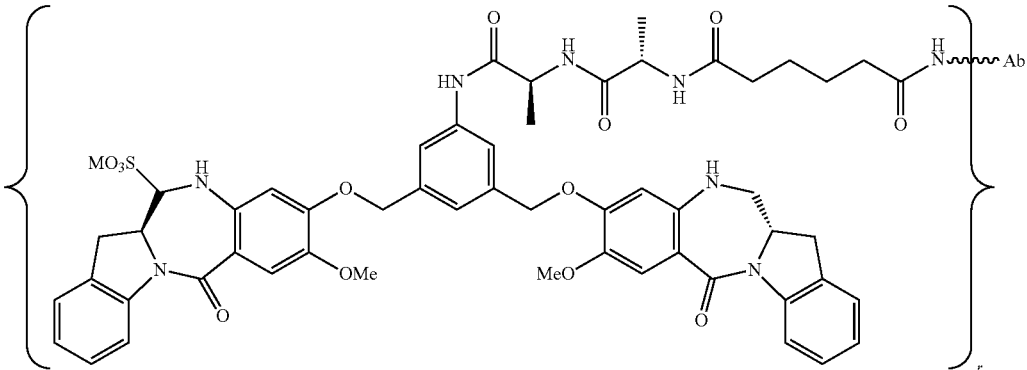

TABLE 2-continued

| Conjugate Name | Conjugate Structure |
|---|---|
| Ab-D3(a) | (structure) |
| Ab-sSPDB-D4 | (structure) |
| Ab-sSPDB-D4(a) | (structure) |
| Ab-Cys-D1 | (structure) |
| Ab-Cys-D1(a) | (structure) |

TABLE 2-continued

| Conjugate Name | Conjugate Structure |
|---|---|
| Ab-Ser-D1 | |
| Ab-Ser-D1(a) | |
| Ab-Cys-DGN462 | |
| Ab-Cys-DGN462(a) | |
| Ab-Ser-DGN462 | |
| Ab-Ser-DGN462(a) | |

TABLE 2-continued

| Conjugate Name | Conjugate Structure |
|---|---|
| Ab-Cys-D5 | |
| Ab-Cys-D5(a) | |
| Ab-Ser-D6 | |
| Ab-Ser-D6(a) | |

Wherein, in Table 2, r is an integer from 1 to 10; Ab-NH is an antibody covalently linked to the compound through a lysine; Ser indicates an antibody linked to the compound through an N-terminal serine; Cys indicates an antibody linked to the compound through a cysteine; and M is $H^+$, $Na^+$, $K^+$, or any pharmaceutically acceptable cation.

This disclosure is also directed to other variations in the linker of the ADCs in Table 2, that are readily apparent to those of ordinary skill in the art. For example, the $SO_3$ M group shown on the linker can be substituted with 'H' to obtain an ADC wherein the antibody Ab is linked via SPDB linker to the cytotoxic compounds D1, D1(a), D2, D2(a), DGN462, DGN462(a), D3, D3(a), D4, D4(a), D5, D5(a), D6, and D6(a), respectively. Such variations and similar variations are encompassed by this disclosure.

In some embodiments, RSA is eliminated in the disclosed compositions. In some embodiments, RSA is decreased by about 90% to 100% in the disclosed compositions. In certain embodiments, RSA is decreased by about 80% to about 90% in the disclosed compositions. In some embodiments, RSA is decreased by about 70% to about 80% in the disclosed compositions. In further embodiments, RSA is decreased by about 60% to about 70% in the disclosed compositions. In still further embodiments, the RSA is decreased by about 50% to about 60% in the disclosed compositions. In yet further embodiments, RSA is decreased by about 40% to about 50% in the disclosed compositions. In some embodiments, RSA is decreased by about 30% to about 40% in the disclosed compositions.

Previous formulations for antibodies or ADCs have been buffered to a pH of approximately 5-6.5 in order to maintain the structure and stability of the antibody or the ADC. Surprisingly, we have discovered that pH can affect the amount and extent of RSA in a solution and, specifically, that a lower than expected pH of approximately 4-4.5, can reduce RSA for an ADC. Another aspect of this disclosure is directed to compositions comprising ADCs comprising a benzodiazepine, wherein the composition has a low pH. It is believed that a lower pH allows for a higher amount of $H^+$ ions that can interact non-covalently with the antibodies in solution and inhibit the antibodies' ability to form oligomeric species through intermolecular interactions, thereby reducing RSA. In some embodiments, the composition has a pH between about 4.0 to about 4.5. One aspect of this disclosure is directed to a composition having a pH between about 4.0 and about 4.5 and comprising a betaine and an ADC comprising a benzodiazepine. In some embodiments, the betaine is trimethlyglycine. Another aspect of this disclosure is directed to a composition having a pH between 4.0 and 4.5 and comprising an amino acid with a hydrophobic side chain and an ADC comprising a benzodiazepine. In some embodiments, the benzodiazepine is a compound in Table 1. In some embodiments, the ADC is an ADC in Table 2.

The compositions of this disclosure are formulated to be acceptable for pharmaceutical use, such as, for example, administration to a human in need thereof. In some embodiments, the ADC is formulated into a composition comprising a physiologically acceptable carrier (e.g., excipient or diluent). Physiologically acceptable carriers are well known and are readily available, and include buffering agents, anti-oxidants, bacteriostats, salts, and solutes that render the composition isotonic with the blood or other bodily fluid of the human patient, and aqueous and non-aqueous sterile suspensions that can include suspending agents, solubilizers, thickening agents, stabilizers (e.g., surfactants), and preservatives. The choice of carrier will be determined, at least in part, by the location of the target tissue and/or cells, and the particular method used to administer the composition. Examples of suitable carriers and excipients for use in ADC pharmaceutical formulations are disclosed in, for example, International (PCT) Patent Application Nos. WO 00/02587, WO 02/060955, and WO 02/092127, and Ghetie et al., *J. Immunol. Methods*, 112, 267-277 (1988).

Pharmaceutically acceptable buffering agents may be used in connection with the disclosed compositions. In some embodiments, succinate may be used as a buffering agent in connection with the disclosed compositions. In other embodiments, citrate may be used as a buffering agent in connection with the disclosed compositions. In some embodiments, sodium bisulfite may be used in addition to succinate or citrate. Other exemplary buffering agents that may be used with the disclosed compositions include acetate and phosphate. The buffering agent may be present in the compositions of this disclosure in any suitable concentration, so long as sufficient stability of the composition is achieved under the desired conditions. In this regard, the concentration of the buffering agent in the composition is about 2 mM to about 50 mM (e.g., about 2-10 mM, about 10-20 mM, about 20-30 mM, about 30-40 mM, or about 40-50 mM). In some embodiments, the concentration of the buffering agent in the composition is about 5-15 mM (e.g., about 10 mM). In some embodiments, the buffering agent is sodium succinate or sodium acetate. In some embodiments, the buffering agent is sodium citrate. The buffering agent typically is present in the disclosed compositions such that the pH is maintained within a desired range.

The compositions of this disclosure also optionally contain a surfactant. Any suitable surfactant can be used. Suitable surfactants are well known to those skilled in the art. In some embodiments, the surfactant is a polysorbate. In some embodiments, the surfactant is polysorbate 20 or polysorbate 80. The surfactant may be present in the compositions of this disclosure in any suitable concentration, so long as sufficient stability of the composition is achieved under the desired conditions. In this regard, the concentration of the surfactant in the composition is about 0.002% to about 0.1% wt./vol. (e.g., about 0.002-0.01%, about 0.005-0.02%, or about 0.01-0.1% wt./vol.) of the total volume of the composition. In some embodiments, the concentration of the surfactant in the composition is about 0.005-0.02% wt./vol. (e.g., about 0.01% wt./vol.) of the total volume of the composition.

The composition of this disclosure can further be stabilized by the addition of sugar. In some embodiments, the sugar is sucrose or trehalose. In some embodiments, the concentration of sucrose or trehalose in the composition is about 0.1% to about 10% wt./vol. (e.g., about 0.1-1%, about 2-5%, or about 7-10% wt./vol.) of the total volume of the composition. The composition can also further comprise bulking agents. In some embodiments, the bulking agent is mannitol. In other embodiments, the bulking agent is glycine.

The compositions of this disclosure can be lyophilized. Lyophilization refers to freeze drying under a vacuum. Lyophilization typically is accomplished by freezing a particular formulation such that the solutes are separated from the solvent(s). The solvent is then removed by sublimation (i.e., primary drying) and next by desorption (i.e., secondary drying). When the compositions of this disclosure are lyophilized and then reconstituted, RSA is still reduced or inhibited. Thus, although the small hydrophobic molecule can be added to compositions prior to lyophilization, the benefits of reduced or inhibited RSA are still realized in the compositions that are reconstituted after lyophilization.

In order to prevent degradation of the composition during freezing and drying, the lyophilized composition optionally further comprises a cryoprotectant. In some embodiments, the cryoprotectant is an amorphous cryoprotectant. The term "cryoprotectant," as used herein, refers to an excipient that protects unstable molecules during freezing. Suitable cryoprotectants for use in the compositions of this disclosure are known to those skilled in the art, and include, for example, glycerol, dimethyl sulfoxide (DMSO), polyethylene glycol (PEG), dextran, glucose, trehalose, and sucrose. In some embodiments, the cryoprotectant is sucrose. The cryoprotectant may be present in the lyophilized composition in any suitable amount. In some embodiments, the lyophilized composition comprises about 0.5 mg to about 5 mg (e.g., about 0.5 mg to about 2 mg) of the cryoprotectant per mg of the conjugate (e.g., about 0.8 mg cryoprotectant per mg of the conjugate. In some embodiments, the lyophilized composition comprises about 2 mg cryoprotectant per mg of the conjugate. In some embodiments, the lyophilized composition comprises about 4 mg cryoprotectant per mg of the conjugate. In some embodiments, the cryoprotectant is sucrose and the lyophilized composition comprises about 0.5 mg to about 2 mg (e.g., about 1 mg) sucrose per mg of the conjugate Lyophilization methods are well known in the art and are described in, for example, Wang, W., *Int. J. Pharm.*, 203, 1-60 (2000). For example, the lyophilized compositions of this disclosure can be produced using a lyophilization cycle comprising the following steps: (1) pre-cooling at a shelf temperature of 4° C. and ambient chamber pressure for 2.5 hours, (2) freezing at a shelf temperature of −50° C. and ambient chamber pressure for 14 hours, (3) glycine recrystallization at a shelf temperature of −20° C. and ambient chamber pressure for 6 hours, (4) re-freezing at a shelf temperature of −50° C. and ambient chamber pressure for 16 hours, (5) primary drying at a shelf temperature of −13° C. and 100 mTorr of pressure for 24 hours, (6) secondary drying at a shelf temperature of 24° C. and 100 mTorr of pressure for 10 hours, and (7) stopper phase at a shelf temperature of 24° C. and ambient chamber pressure. However, lyophilized compositions of this disclosure are not limited to compositions produced by the above-described method. Indeed, any suitable lyophilization method can be used to produce the lyophilized compositions of this disclosure, and it will be apparent to those skilled in the art that the chosen lyophilization parameters (e.g., drying times) will vary depending on a variety of factors, including the volume of the solution to be lyophilized.

The compositions of this disclosure are advantageous over the prior art formulations for many reasons. The increase in the amount of monomer results in compositions of increased potency. Efficacy is increased because each composition delivers greater therapeutic effect per dose. This is advantageous because it reduces the number of doses that subjects need.

In addition to the increased potency, the compositions of this disclosure also decrease toxicity, hence improving patient safety. The compositions of this disclosure deliver more of the cytotoxic compounds to the targeted sites by virtue of the reduced RSA, thereby reducing the amount of cytotoxic compounds that can interact with non-targeted sites. Furthermore, the reduced RSA decreases the viscosity of a solution, thereby improving the efficacy of some modes of administration because the disclosed compositions are less likely to clog or impede the plunger of a syringe.

Methods of Treating

This disclosure is also directed to methods of treating cancer in a subject comprising administering to the subject a composition comprising (a) an effective amount of an ADC comprising a benzodiazepine and (b) a small hydrophobic molecule selected from the group consisting of betaines and amino acids with hydrophobic side chains, wherein the ADC is cytotoxic in one or more cells, thereby treating the cancer. In some embodiments, the composition has a pH of about 4.0 to about 4.5. The descriptions of the ADCs comprising a benzodiazepine, the small hydrophobic molecules, excipients (e.g., buffering agents, surfactants, sugars, etc.), and other components described herein are also applicable to the compositions that are used in the methods of treating.

While any suitable means of administering the composition to a subject can be used, in some embodiments, the disclosed compositions are administered to a human via injection. In some embodiments, the disclosed compositions are administered to a human via infusion. As used herein, the term "injection" refers to the forceful introduction of the disclosed compositions into a target tissue of the human. As used herein, the term "infusion" refers to the introduction of the disclosed compositions into a tissue, e.g., a vein, of the human. The composition can be administered to the human by any suitable route. In some embodiments, the compositions are administered to the human intravenously or intraperitoneally. In some embodiments, administration is intratumoral. When the composition is administered by injecting, any suitable injection device can be used to administer the composition. For example, the common medical syringe can be used to directly inject the composition into a subcutaneous tumor. Alternatively, the composition can be topically applied to the tumor by bathing the tumor in the disclosed liquid composition. Likewise, the tumor can be perfused with the disclosed composition over a period of time using any suitable delivery device, e.g., a catheter. Other routes of administration can be used to deliver the composition to the human. Some routes can provide a more immediate and more effective reaction than other routes. In some embodiments, the composition is administered to a surface of the subject selected from the group of dermal and mucosal surfaces and combinations thereof. For example, the disclosed compositions can be applied or instilled into body cavities, absorbed through the skin, inhaled, or administered parenterally via, for instance, intramuscular or intraarterial administration. In some embodiments, the disclosed compositions parenterally administered to a human are specifically targeted to particular cells, e.g., cancer cells.

Methods of Formulating

This disclosure is also directed to methods of formulating, comprising providing an ADC comprising a benzodiazepine in an aqueous solution, adding to the aqueous solution comprising the ADC a small hydrophobic molecule selected from the group consisting of betaines and amino acids with hydrophobic side chains. In some embodiments, the method further comprises adjusting the pH of the aqueous solution to between about 4.0 and about 4.5. In some embodiments, the method further comprises lyophilizing the solution. In some embodiments, the method further comprises reconstituting the lyophilized composition.

In further embodiments of the method, the addition of a small hydrophobic molecule reduces RSA in the aqueous solution by about 30% to about 40%. In some embodiments, the addition of a small hydrophobic molecule reduces RSA in the aqueous solution by about 40% to about 50%. In certain embodiments, the addition of a small hydrophobic molecule reduces RSA in the aqueous solution by about 50% to about 60%. In further embodiments, the addition of a small hydrophobic molecule reduces RSA in the aqueous solution by about 60% to about 70%. In still further embodiments, the addition of a small hydrophobic molecule reduces RSA in the aqueous solution by about 70% to about 80%. In yet further embodiments, the addition of a small hydrophobic molecule reduces RSA in the aqueous solution by about 80% to about 90%. In some embodiments, the addition of a small hydrophobic molecule reduces RSA in the aqueous solution by about 90% to 100%. In still further embodiments, the addition of a small hydrophobic molecule eliminates RSA in the aqueous solution. In some embodiments, the amount of RSA is measured by multiangle light scattering. In some further embodiments, the amount of RSA is measured by dynamic light scattering.

In some embodiments, the method further comprises lyophilizing the aqueous solution, thereby obtaining a lyophilized composition. In certain embodiments, the method further comprises reconstituting the lyophilized composition, thereby creating a reconstituted lyophilized composition. In further embodiments of the method, the addition of a small hydrophobic molecule reduces RSA in the reconstituted lyophilized composition by about 30% to about 40%. In some embodiments, the addition of a small hydrophobic molecule reduces RSA in the reconstituted lyophilized composition by about 40% to about 50%. In certain embodiments, the addition of a small hydrophobic molecule reduces RSA in the reconstituted lyophilized composition by about 50% to about 60%. In further embodiments, the addition of a small hydrophobic molecule reduces RSA in the reconstituted lyophilized composition by about 60% to about 70%. In still further embodiments, the addition of a small hydrophobic molecule reduces RSA in the reconstituted lyophilized composition by about 60% to about 70%. In yet further embodiments, the addition of a small hydrophobic molecule reduces RSA in the reconstituted lyophilized composition by about 70% to about 80%. In some embodiments, the addition of a small hydrophobic molecule reduces RSA in the reconstituted lyophilized composition by about 80% to about 90%. In certain embodiments, the addition of a small hydrophobic molecule reduces RSA in the reconstituted lyophilized composition by about 90% to 100%. In some embodiments, the addition of a small hydrophobic molecule eliminates RSA in the reconstituted lyophilized composition.

The descriptions of the ADCs comprising a benzodiazepine, the small hydrophobic molecules, excipients (e.g., buffering agents, surfactants, sugars, etc.), and other components described herein are also applicable to the compositions that are used in the methods of treating.

Methods of Reducing RSA

This disclosure is also directed to methods of reducing RSA in ADCs comprising benzodiazepines. One aspect is directed to methods of reducing RSA in an ADC comprising a benzodiazepine, the method comprising providing an ADC comprising a benzodiazepine in an aqueous solution, wherein the ADC exhibits RSA, adding to the aqueous solution a small hydrophobic molecule selected from the group consisting of betaines and amino acids with hydrophobic side chains, wherein the small hydrophobic molecule reduces or inhibits RSA. In some embodiments, the method further comprises detecting reversible self-association. In certain embodiments, the method further comprises lyophilizing the aqueous solution. In further embodiments, the method further comprises reconstituting a lyophilized composition.

In some embodiments, RSA is eliminated in the disclosed compositions. In some embodiments, RSA is decreased by about 90% to 100% in the disclosed compositions. In certain embodiments, RSA is decreased by about 80% to about 90% in the disclosed compositions. In some embodiments, RSA is decreased by about 70% to about 80% in the disclosed compositions. In further embodiments, RSA is decreased by about 60% to about 70% in the disclosed compositions. In still further embodiments, the RSA is decreased by about 50% to about 60% in the disclosed compositions. In yet further embodiments, RSA is decreased by about 40% to about 50% in the disclosed compositions. In some embodiments, RSA is decreased by about 30% to about 40% in the disclosed compositions. In some embodiments, the method further comprises adjusting the pH of the solution to between about 4.0 to about 4.5.

The descriptions of the ADCs comprising benzodiazepine, the small hydrophobic molecules, excipients (e.g., buffering agents, surfactants, sugars, etc.), and other components described herein are also applicable to the compositions that are used in the methods of reducing RSA.

EXAMPLES

Example 1: Examination of RSA

This example demonstrates the use of dynamic light scattering and sedimentation velocity analytical ultracentrifugation as techniques for evaluating the extent of reversible self-association in an indolinobenzodiazepine ADC, huMy9-6-DGN462.

Dynamic Light Scattering measures the time-dependent fluctuation in the intensity of light scattered from the proteins or antibodies in solution at a fixed scattering angle. As the protein or antibody or ADC molecules undergo Brownian motion, their relative positions change with time. Small molecules, which diffuse quickly, generate signals that fluctuate rapidly, while larger proteins and antibodies generate slower signal fluctuations. The translational diffusion coefficient, $D_t$, is related to the intensity autocorrelation function of the time-dependent fluctuation in intensity. The hydrodynamic diameter can be determined using the Stokes-Einstein relation [$d_h = K_T/3\pi\eta D_t$, where $d_h$ is the hydrodynamic diameter, $K_T$ is the Boltzmann constant, $\eta$ is viscosity, and $D_t$ is the translational diffusion coefficient]. Scattering intensity data are processed using DLS instrument software to determine the value for the translational diffusion coefficient and the size distribution of the scattering molecules, i.e., the protein or antibody specimen.

All proteins will aggregate to some extent during quiescent storage as the result of exposure of hydrophobic patches from partial unfolding that occurs with fluctuations between the native and non-native states. These aggregates do not dissociate with changes in pH or dilution, but require the introduction of chaotropes such as guanidine or urea to dissociate. When examined by dynamic light scattering techniques solutions that contain small amounts of aggregated protein, do not look substantially different than a solution of pure monomeric protein, i.e., the hydrodynamic diameter and diffusion coefficients remain relatively constant regardless of solution characteristics such as concentration.

However, in the case of reversible self-association, where a change in the solution properties, such as dilution, can effect a change in the association state (i.e., disrupt the self-association), DLS can be used to measure a unique diffusion coefficient for a given concentration. A plot of translational diffusion coefficient against protein or antibody concentration yields a best fit line with slope m and a y-intercept, b. A line where the slope m, is positive indicates a net repulsive interaction of the proteins or antibodies, while a negative slope is indicative of a net attractive interaction. This can be seen in FIG. 1.

Sedimentation velocity analytical ultracentrifugation (SV-AUC) measures the rate at which molecules in solution move in response to centrifugal force generated in a centrifuge. In SV-AUC the sample is spun at a very high speed (42-60 k rpm) and the evolution of the concentration gradient is monitored by UV absorbance optics. The high centrifugal force rapidly depletes the protein or antibody from the center of the rotor and forms a boundary that moves towards the outside of the rotor over time. The rate that this boundary moves is a measure of the sedimentation coefficient and is related to the molecular weight and molecular shape, generally represented by the equation $s = m/6\pi\eta r_0$ where m is molecular weight, $\eta$ is viscosity, and $r_0$ is the radius of the particle. From these data a distribution of the variously sized components in the sample can be measured.

The rate at which the boundary moves is also dependent on the diffusion and frictional forces that act in the opposite direction of sedimentation of the molecule. The minimum width of the sedimentation boundary is related to the diffusion coefficient. The presence of several species with similar sedimentation coefficients will cause the boundary to be broader than expected.

In the case of reversibly self-associating molecules, the sedimentation boundary is broader than expected due to the presence of higher ordered oligomers that are stable over the time scale of sedimentation. This manifests as diffusion that is much faster than would be expected for molecules of the measured sedimentation coefficients. To account for this, the shape of the molecule, which is inferred from the frictional ratio $f/f_0$, where f is the frictional coefficient for the protein or antibody and $f_0$ is the frictional coefficient for a hard solid sphere of radius r, is calculated to be more spherical. For reversibly self-associating antibodies which are more elongated than globular, the frictional ratio is considerably smaller (~1) than for non-associating antibodies (~1.5).

Figure 2A:
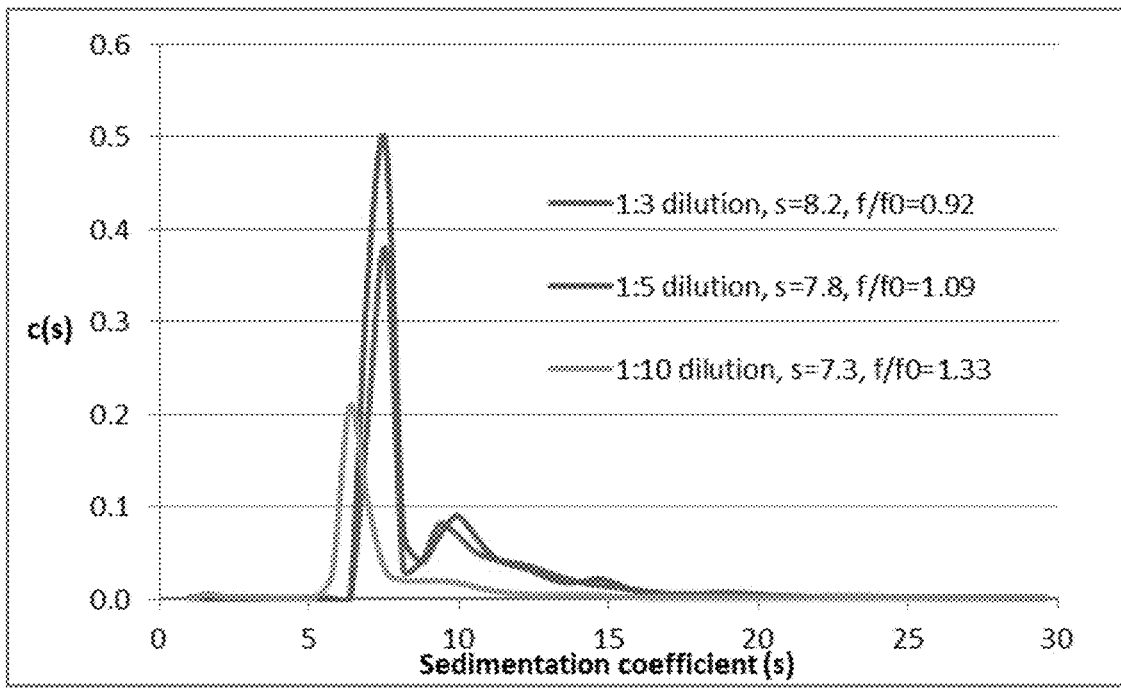
FIGS. 2A and 2B show the SV-AUC distribution of a reversibly self-associating system using huM9-6-sSPDB-DGN462 as an example.
Figure 2B:
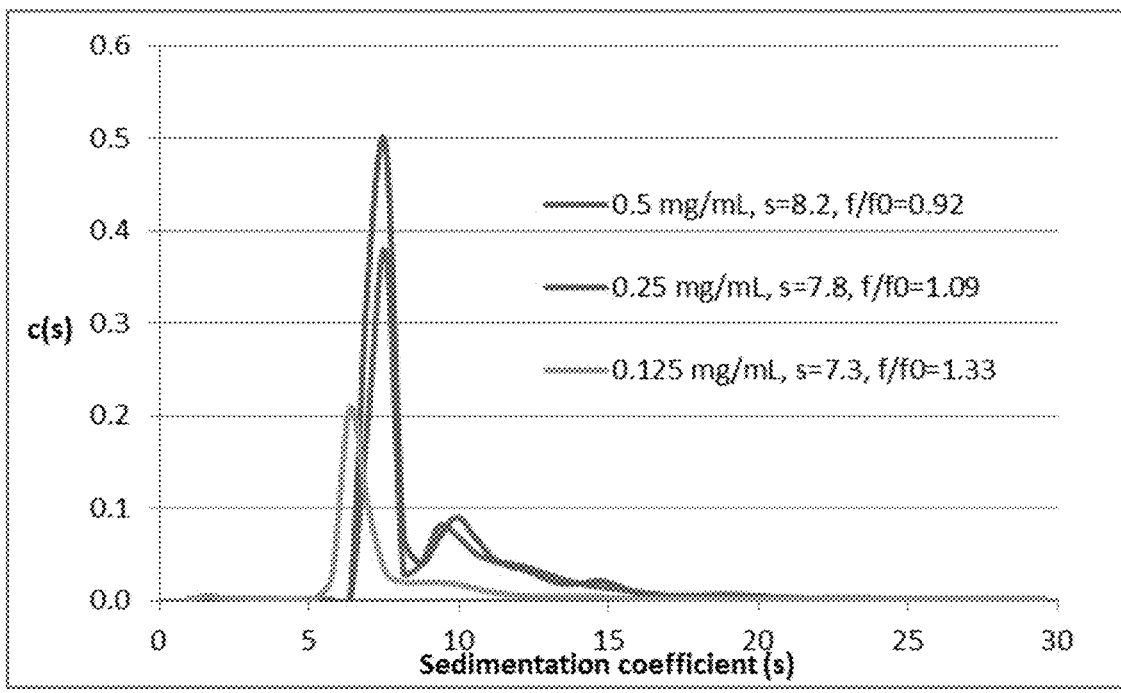

In the case of reversibly self-associating molecules, there is also a concentration dependent measure of the distribution of the components in the sample. In SV-AUC, when a set of serially diluted samples is run, the relative proportions of the components change as well as the measured sedimentation coefficient. As the solution becomes more dilute, the sedimentation coefficient begins to approach the expected value. In the case of antibodies this is ~6.5 s. This can be seen in FIGS. 2A & 2B.

Example 2a: Influence of Drug Load on RSA

This Example Demonstrates the Impact of Drug Load (DAR) on the Extent of reversible self-association in an indolinobenzodiazepine ADC. DAR represents an average of indolinobenzodiazepine molecules attached to the antibodies.

Conjugates comprising the huMy-9-6 monoclonal antibody chemically coupled to the indolinobenzodiazepine DGN462 via a 4-(2-pyridinyldithio)-2-sulfo-,1-(2,5-dioxo-1-pyrrolidinyl) butanoic acid ester (sSPDB) linker (the ADC is referred to as "huMy9-6-sSPDB-DGN462") were prepared using methods described herein and known in the art (see, e.g., U.S. Pat. No. 8,889,669, which is herein incorporated by reference) to yield drug to antibody ratios (DAR) of 1.8, 2.4, and 2.8. huMy9-6-sSPDB-DGN462 conjugates with differing drug loads, but the same antibody concentration (about 2 mg/mL), were formulated in 20 mM histidine, 8% trehalose, 0.02% polysorbate 20, pH 6.1.

Figure 3:
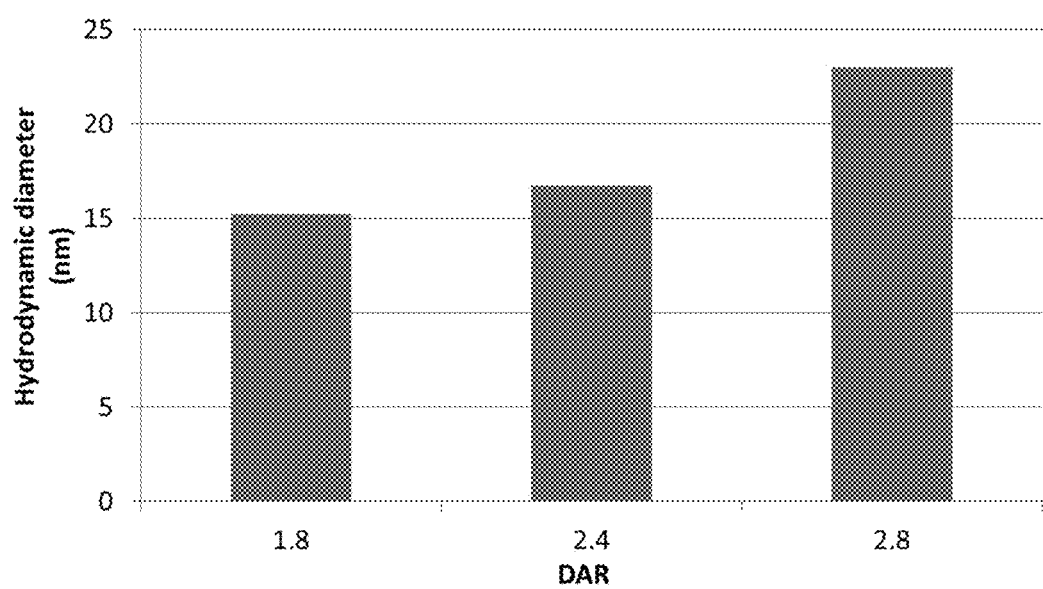
FIG. 3 shows the changes in hydrodynamic diameter in relation to drug-to-antibody ratio as measured by dynamic light scattering.

As can be seen in FIG. 3, compositions with a lower drug load had smaller hydrodynamic diameters than those with higher drug loads suggesting that the intermolecular interactions are between the indolinobenzodiazepine moieties attached to each antibody.

Example 2b: Reduced RSA Compositions

This example demonstrates the production of a composition that reduces or inhibits reversible self-association comprising an ADC comprising an antibody chemically coupled to an indolinobenzodiazepine (DGN462), buffering agent, surfactant, hydrophobic amino acid, sugar, and water.

Figure 4:
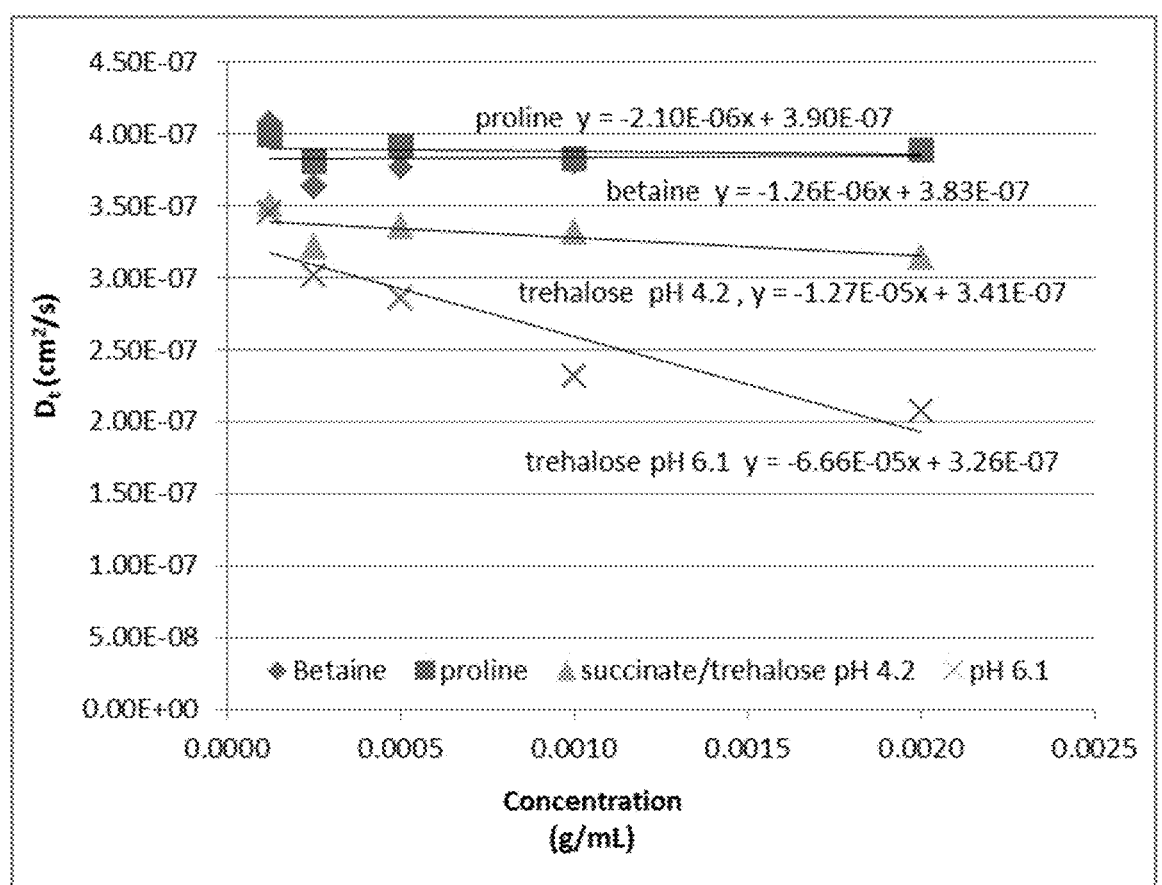
FIG. 4 shows the dynamic light scattering plot of different ADC compositions.
Figure 5:
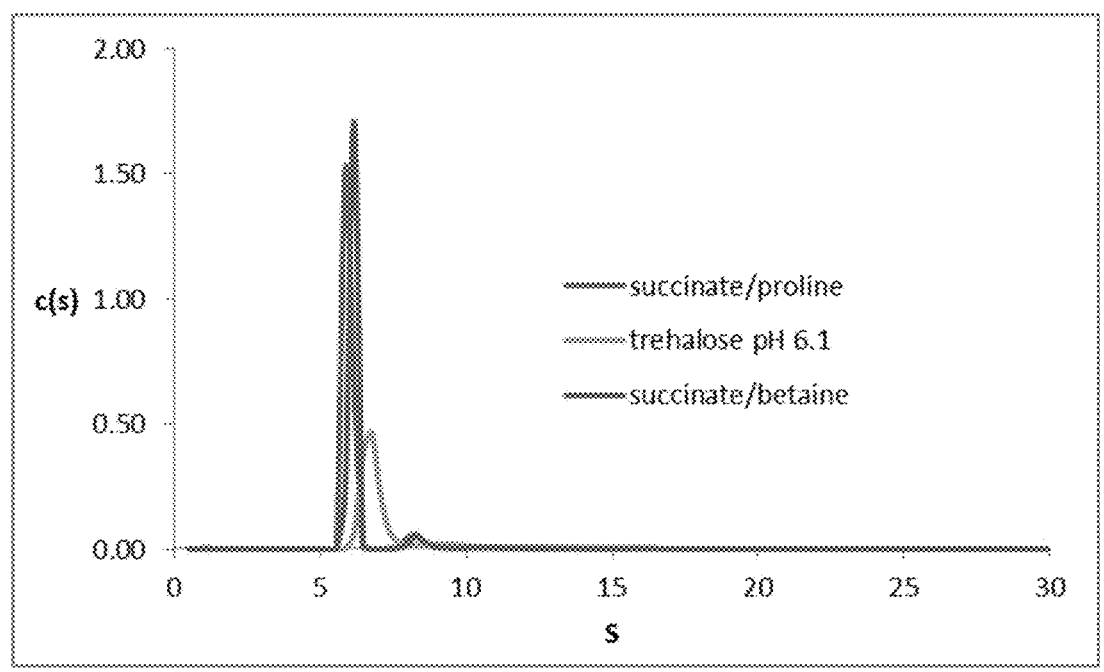
FIG. 5 shows the SV-AUC distribution of different ADC compositions.

A conjugate comprising the huMy-9-6 monoclonal antibody chemically coupled to the indolinobenzodiazepine DGN462 via a 4-(2-pyridinyldithio)-2-sulfo-,1-(2,5-dioxo-1-pyrrolidinyl) butanoic acid ester (sSPDB) linker (the ADC is referred to as "huMy9-6-sSPDB-DGN462") was prepared using methods described herein and known in the art (see, e.g., U.S. Pat. No. 8,889,669). huMy-9-6-sSPDB-DGN462 conjugates were formulated as follows: (a) 0.2 mg/mL ADC, 20 mM histidine, 8% trehalose, 0.02% polysorbate 20, pH 6.1; (b) 0.2 mg/mL ADC, 10 mM succinate, 8% trehalose, pH 4.2; (c) 0.5 mg/mL ADC, 10 mM sodium succinate, 280 mM betaine, pH 4.2; and (d) 0.5 mg/mL ADC, 10 mM sodium succinate, 280 mM proline, pH 4.2. The results of analysis of dynamic light scattering demonstrating the effects of the formulation pH and excipients on reversible self-association are set forth in FIG. 4. As can be seen in FIG. 4, the formulations with proline and betaine have the least negative slope, indicating a lower amount of net attractive interaction when compared to the other formulations. The results of SV-AUC for the 10 mM succinate, 280 mM proline formulation and the 10 mM succinate, 280 mM betaine formulation are set forth in FIG. 5. The results show that succinate/proline or succinate/betaine formulations are superior to trehalose/histidine pH 6.1 formulations for reducing RSA.

These experiments demonstrate the surprisingly reduced RSA in the compositions of this disclosure.

Example 3a: Reduced RSA Formulation: AbX-D2 Conjugate with Proline

This example demonstrates the production of a composition for reducing or inhibiting reversible self-association comprising a conjugate comprising an antibody chemically coupled to an indolinobenzodiazepine D2, buffering agent, surfactant, hydrophobic amino acid, sugar, and water.

A conjugate comprising a monoclonal antibody AbX chemically coupled to the indolinobenzodiazepine D2 (herein referred to as "AbX-D2") is prepared using methods described herein and in U.S. Application Publication No. US20160082114A1, which is herein incorporated by reference in its entirety. Compositions comprising the AbX-D2 conjugate are formulated as follows: (a) 20 mM histidine, 8% trehalose, 0.02% polysorbate 20, pH 6.1; (b) 10 mM acetate, 8% trehalose, pH 4.2; (c) 10 mM sodium succinate, 280 mM proline or 280 mM Betaine, pH 4.2; and (d) 10 mM sodium succinate, 8% trehalose, and optionally 0.02% polysorbate, pH4.2. For each of the compositions, 2-200 µM bisulfate may also be included.

Example 3b: Reduced RSA Formulation: huMov19-sSPDB-D1 Conjugate with Leucine

This example demonstrates the production of a composition for reducing or inhibiting reversible self-association comprising a conjugate comprising an antibody chemically coupled to an indolinobenzodiazepine D3, buffering agent, surfactant, hydrophobic amino acid, sugar, and water.

A conjugate comprising the huMov19 monoclonal antibody chemically coupled to the indolinobenzodiazepine D1 (herein referred to as "huMov19-sSPDB-D1") is prepared using methods described herein (see, e.g., U.S. Application Publication No. US20160106863). Compositions comprising the huMov19-sSPDB-D1 conjugate are formulated as follows: (a) 20 mM histidine, 8% trehalose, 0.02% polysorbate 20, pH 6.1; (b) 10 mM acetate, 8% trehalose, pH 4.2; (c) 10 mM sodium succinate, 125 mM leucine, pH 4.2; and (d) 10 mM sodium succinate, 8% trehalose, and optionally 0.02% polysorbate, pH4.2.

Example 3c: Reduced RSA Formulation: huMov19-sSPDB-D4 Conjugate with Isoleucine

This example demonstrates the production of a composition for reducing or eliminating reversible self-association comprising a conjugate comprising an antibody chemically coupled to an indolinobenzodiazepine D4, buffering agent, surfactant, hydrophobic amino acid, sugar, and water.

A conjugate comprising the huMov19 monoclonal antibody chemically coupled to the indolinobenzodiazepine D4 (herein referred to as "huMov19-sSPDB-D4") is prepared using methods described herein (see, e.g., U.S. Application Publication No: US20160082114A1). Compositions comprising the huMov19-sSPDB-D4 conjugate are formulated as follows: (a) 20 mM histidine, 8% trehalose, 0.02% polysorbate 20, pH 6.1; (b) 10 mM acetate, 8% trehalose, pH 4.2; (c) 10 mM sodium succinate, 125 mM isoleucine, pH 4.2; and (d) 10 mM sodium succinate, 8% trehalose, and optionally 0.02% polysorbate, pH4.2.

Example 4: Methods of Making D1

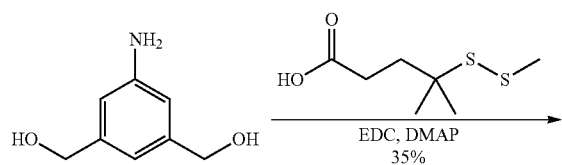

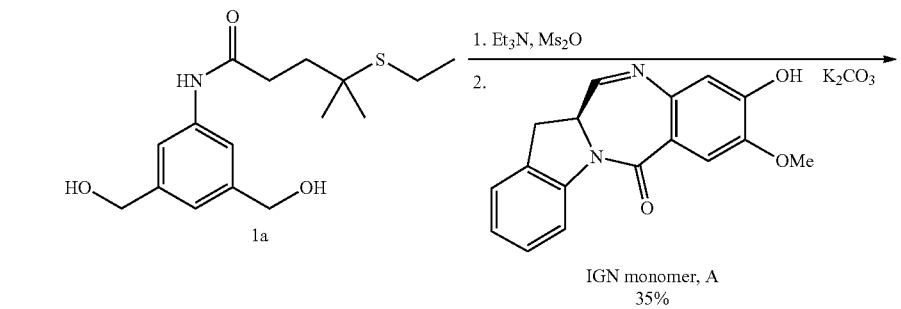

Compound 1a: To a stirred solution of (5-amino-1,3-phenylene)dimethanol (1.01 g, 6.59 mmol) in anhydrous dimethylformamide (16.48 mL) and anhydrous tetrahydrofuran (16.48 ml) was added 4-methyl-4-(methyldisulfanyl)pentanoic acid (1.281 g, 6.59 mmol), N-(3-dimethylaminopropyl)-N'-ethylcarbodiimide hydrochloride (2.53 g, 13.19 mmol), and 4-dimethylaminopyridine (0.081 g, 0.659 mmol). The resulting mixture was stirred for 18 hours at room temperature. The reaction was quenched with saturated ammonium chloride solution and extracted with ethyl acetate (3×50 mL). The organic extracts were washed with water and brine, then dried over anhydrous sodium sulfate. The solution was filtered and concentrated in vacuo and the resulting residue was purified by silica gel chromatography (Ethyl acetate/Hexanes) to obtain compound 1a as a white solid (0.70 g, 32% yield). $^1$H NMR (400 MHz, DMSO-d6: δ 9.90 (s, 1H), 7.43 (s, 2H), 6.93 (s, 1H), 5.16 (t, 2H, J=5.7 Hz), 4.44 (d, 4H, J=5.7 Hz), 2.43 (s, 3H), 2.41-2.38 (m, 2H), 1.92-1.88 (m, 2H), 1.29 (s, 6H). MS (m/z), found 330.0 $(M+1)^+$.

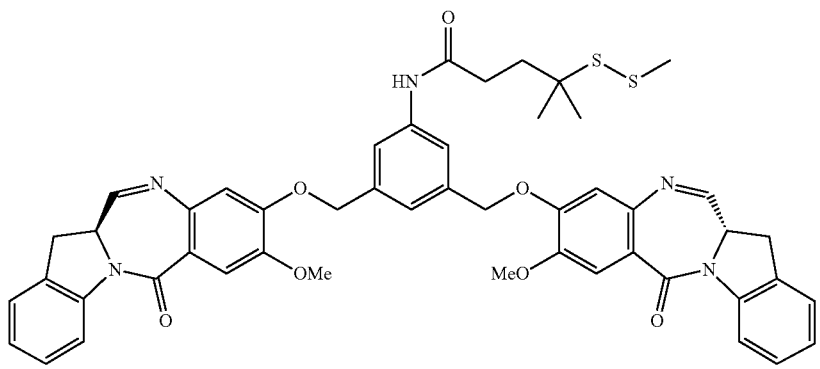

Compound 1b: To a cooled (−10° C.) solution of compound 1a (219 mg, 0.665 mmol) in anhydrous dichloromethane (6.65 mL) was added triethylamine (463 µl, 3.32 mmol) followed by dropwise addition of methanesulfonic anhydride (298 mg, 1.662 mmol). The mixture stirred at −10° C. for 2 hours, then the mixture was quenched with ice water and extracted with cold ethyl acetate (2×30 mL). The organic extracts were washed with ice water, dried with anhydrous sodium sulfate, filtered and concentrated under reduced pressure to obtain the crude dimesylate.

The crude dimesylate (227 mg, 0.467 mmol) and IGN monomer A (303 mg, 1.028 mmol) were dissolved in anhydrous DMF (3.11 mL). Potassium carbonate (161 mg, 1.169 mmol) was added and the mixture stirred for 18 hours at room temperature. Deionized water was added and the resulting precipitate was filtered and rinsed with water. The solid was re-dissolved in dichloromethane and washed with water. The organic layer was dried with anhydrous magnesium sulfate, filtered, and concentrated. The crude residue was purified by silica gel chromatography (Methanol/Dichloromethane) to give compound 1b (227 mg, 36% yield). MS (m/z), found 882.5 (M+1)+.

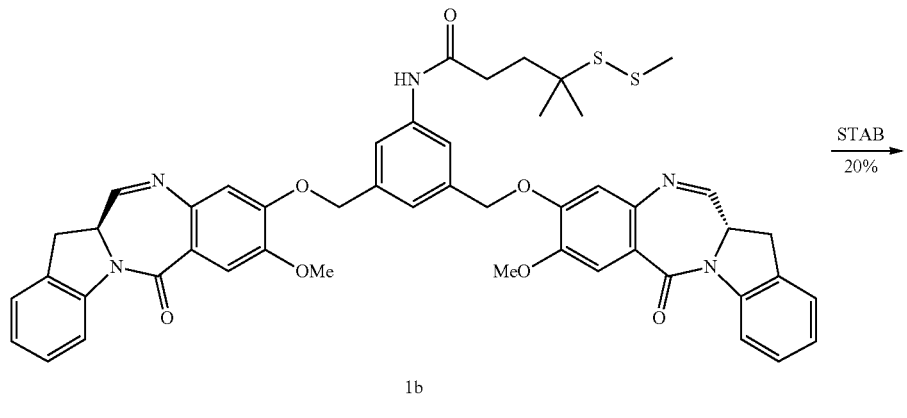

1b

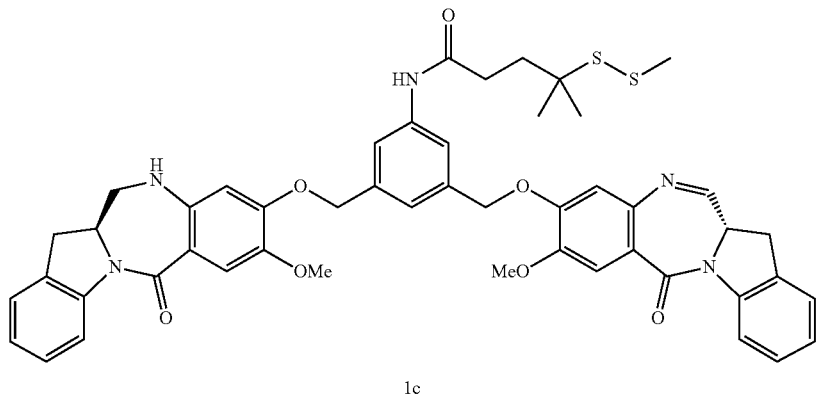

1c

Compound 1c: To a suspension of compound 1b (227 mg, 0.167 mmol) in anhydrous 1,2-dichloroethane (3.346 mL) was added sodium triacetoxyborohydride (STAB) (37.3 mg, 0.167 mmol). The mixture was stirred at room temp for one hour upon which it was quenched with saturated ammonium chloride solution. The mixture was extracted with dichloromethane and washed with brine. The organic layer was dried with anhydrous magnesium sulfate, filtered and concentrated. The crude residue was purified by RP-HPLC (C18, Water/Acetonitrile). Fractions containing desired product were extracted with dichloromethane, dried with anhydrous magnesium sulfate, filtered and concentrated to give compound 1c (35 mg, 19% yield). MS (m/z), found 884.3 (M+1)$^+$.

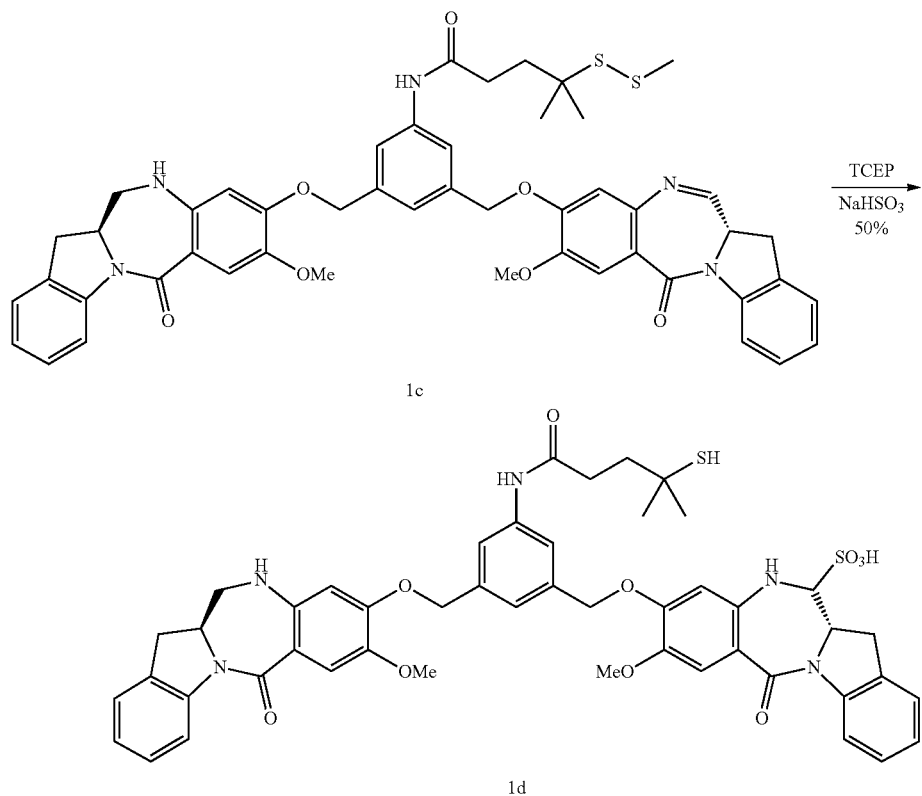

Compound 1d: To a solution of compound 1c (18 mg, 0.017 mmol) in acetonitrile (921 µL) and methanol (658 µL) was added tris(2-carboxyethyl)phosphine hydrochloride (TCEP) (17.51 mg, 0.060 mmol) (neutralized with saturated sodium bicarbonate solution (0.2 mL) in sodium phosphate buffer (132 µL, 0.75 M, pH 6.5). The mixture was stirred at room temperature for 3.5 hours, then diluted with dichloromethane and deionized water. The organic layer was separated, washed with brine, dried with anhydrous sodium sulfate, filtered and concentrated under reduced pressure to obtain the crude thiol. MS (m/z), found 838.3 (M+1)$^+$.

The crude thiol from step 5 (15.5 mg, 0.018 mmol) was dissolved in 2-propanol (1.23 mL). Deionized water (617 µL) and sodium bisulfite (5.77 mg, 0.055 mmol) were added and the mixture stirred for five hours at room temperature. The reaction was frozen in an acetone/dry ice bath, lyophilized, and purified by RP-HPLC (C18, deionized water/ acetonitrile). Fractions containing desired product were frozen and lyophilized to give compound (12S,12aS)-9-((3-(4-mercapto-4-methylpentanamido)-5-((((R)-8-methoxy-6-oxo-11,12,12a,13-tetrahydro-6H-benzo[5,6][1,4]diazepino[1,2-a]indol-9-yl)oxy)methyl)benzyl)oxy)-8-methoxy-6-oxo-11,12,12a,13-tetrahydro-6H-benzo[5,6][1,4]diazepino[1,2-a]indole-12-sulfonic acid (compound 1d, also referred to herein as D1) (6.6 mg, 39% yield). MS (m/z), found 918.2 (M−1)$^−$.

Example 5: Preparation of huMOV19-sulfo-SPDB-1d

A reaction containing 2.0 mg/mL huMOV19 antibody and 6 molar equivalents of sulfo-SPDB-1d in situ mixture by linker in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C. The in situ mixture was prepared by reacting 1.5 mM sulfo-SPDB linker with 1.95 mM of compound 1d in 100% DMA for 4 hours in the presence of 10 mM N,N-Diisopropylethyl amine (DIPEA). Free thiol was then capped by adding a 3-fold excess of maleimidopropionic acid.

Post-reaction, the conjugate was purified and buffer exchanged into 100 mM Arginine, 20 mM Histidine, 2% sucrose, 0.01% Tween-20, 50 µM sodium bisulfite formulation buffer pH 6.1 using NAP desalting columns (Illustra Sephadex G-25 DNA Grade, GE Healthcare). Dialysis was performed in the same buffer for 20 hours at 4° C. utilizing Slide-a-Lyzer dialysis cassettes (ThermoScientific 20,000 MWCO).

The purified conjugate was found to have an average of 2.5 molecules of compound 1d linked per antibody (by UV-Vis using molar extinction coefficients $\varepsilon_{330\ nm}$=15,280 cm$^{-1}$M$^{-1}$ and $\varepsilon_{280\ nm}$=30, 115 cm$^{-1}$M$^{-1}$ for compound 1d, and $\varepsilon_{280\ nm}$=201,400 cm$^{-1}$M$^{-1}$ for huMOV19 antibody), 95% monomer (by size exclusion chromatography), <0.1% unconjugated compound 1d (by acetone precipitation, reverse-phase HPLC analysis) and a final protein concentration of 1.8 mg/ml. The conjugated antibody was found to be >80% intact by gel chip analysis.

Example 6: Methods of Making D2

Synthesis of 2,5-dioxopyrrolidin-1-yl 6-(((S)-1-(((S)-1-((3-(((((S)-8-methoxy-6-oxo-11,12,12a,13-tetrahydro-6H-benzo[5,6][1,4]diazepino[1,2-a]indol-9-yl)oxy)methyl)-5-(((((R)-8-methoxy-6-oxo-12a,13-dihydro-6H-benzo[5,6][1, 4]diazepino[1,2-a]indol-9-yl)oxy)methyl) phenyl)amino)-1-oxopropan-2-yl)amino)-1-oxopropan-2-yl)amino)-6-oxohexanoate, compound 90, also referred to herein as D2.

δ 7.38-7.31 (m, 5H), 6.53-6.42 (m, 1H), 5.42-5.33 (m, 1H), 5.14 (s, 2H), 4.48-4.41 (m, 1H), 4.32-4.20 (m, 1H), 1.49 (s, 9H), 1.42 (d, 3H, J=6.8 Hz), 1.38 (d, 3H, J=7.2 Hz).

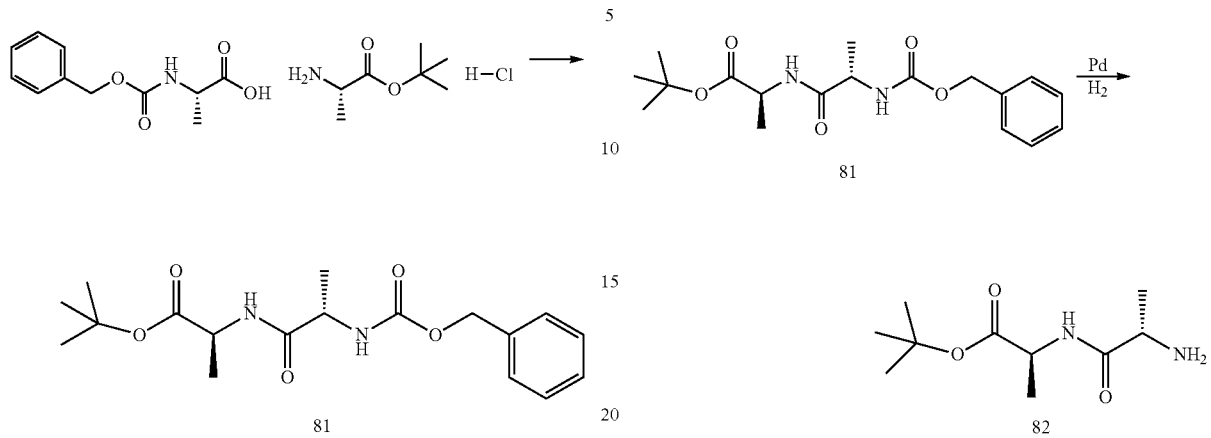

Step 1: (S)-2-(((benzyloxy)carbonyl)amino)propanoic acid (5 g, 22.40 mmol) and (S)-tert-butyl 2-aminopropanoate hydrochloride (4.48 g, 24.64 mmol) were dissolved in anhydrous DMF (44.8 mL). EDC.HCl (4.72 g, 24.64 mmol), HOBt (3.43 g, 22.40 mmol), and DIPEA (9.75 mL, 56.0 mmol) were added. The reaction stirred under argon, at room temperature, overnight. The reaction mixture was diluted with dichloromethane and then washed with saturated ammonium chloride, saturated sodium bicarbonate, water, and brine. The organic layer was dried over sodium sulfate and concentrated. The crude oil was purified via silica gel chromatography (Hexanes/Ethyl Acetate) to yield compound 81 (6.7 g, 85% yield). $^1$H NMR (400 MHz, CDCl$_3$):

Step 2: Compound 81 (6.7 g, 19.12 mmol) was dissolved in methanol (60.7 mL) and water (3.03 mL). The solution was purged with argon for five minutes. Palladium on carbon (wet, 10%) (1.017 g, 0.956 mmol) was added slowly. The reaction was stirred overnight under an atmosphere of hydrogen. The solution was filtered through Celite, rinsed with methanol and concentrated. It was azeotroped with methanol and acetonitrile and the resulting oil was placed directly on the high vacuum to give compound 82 (4.02 g, 97% yield) which was used directly in the next step. $^1$H NMR (400 MHz, CDCl$_3$): δ 7.78-7.63 (m, 1H), 4.49-4.42 (m, 1H), 3.55-3.50 (m, 1H), 1.73 (s, 2H), 1.48 (s, 9H), 1.39 (d, 3H, J=7.2 Hz), 1.36 (d, 3H, J=6.8 Hz).

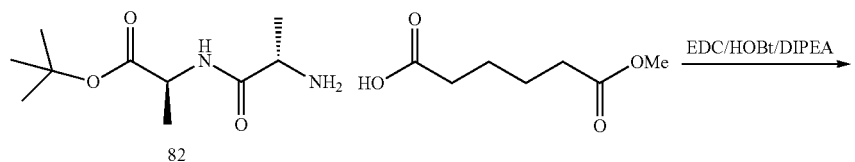

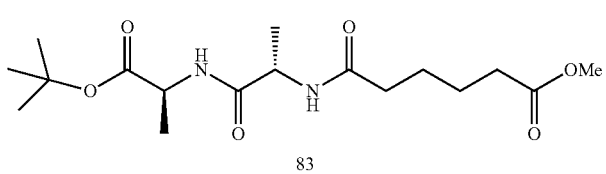

Step 3: Compound 82 (4.02 g, 18.59 mmol) and mono methyladipate (3.03 mL, 20.45 mmol) were dissolved in anhydrous DMF (62.0 mL). EDC.HCl (3.92 g, 20.45 mmol), HOBt (2.85 g, 18.59 mmol) and DIPEA (6.49 mL, 37.2 mmol) were added. The mixture was stirred overnight at room temperature. The reaction was diluted with dichloromethane/methanol (150 mL, 5:1) and washed with saturated ammonium chloride, saturated sodium bicarbonate, and brine. It was dried over sodium sulfate, filtered and stripped. The compound was azeotroped with acetonitrile (5×), then pumped on the high vacuum at 35° C. to give compound 83 (6.66 g, 100% yield). The crude material was taken onto next step without purification. $^1$H NMR (400 MHz, CDCl$_3$): δ 6.75 (d, 1H, J=6.8 Hz), 6.44 (d, 1H, J=6.8 Hz), 4.52-4.44 (m, 1H), 4.43-4.36 (m, 1H), 3.65 (s, 3H), 2.35-2.29 (m, 2H), 2.25-2.18 (m, 2H), 1.71-1.60 (m, 4H), 1.45 (s, 9H), 1.36 (t, 6H, J=6.0 Hz).

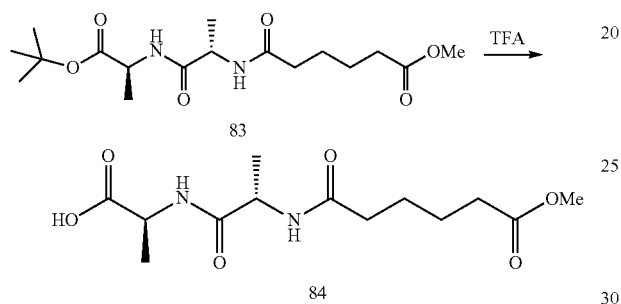

Step 4: Compound 83 (5.91 g, 16.5 mmol) was stirred in TFA (28.6 mL, 372 mmol) and deionized water (1.5 mL) at room temperature for three hours. The reaction mixture was concentrated with acetonitrile and placed on high vacuum to give crude compound 84 as a sticky solid (5.88 g, 100% yield). $^1$H NMR (400 MHz, CDCl$_3$): δ 7.21 (d, 1H, J=6.8 Hz), 6.81 (d, 1H, J=7.6 Hz), 4.69-4.60 (m, 1H), 4.59-4.51 (m, 1H), 3.69 (s, 3H), 2.40-2.33 (m, 2H), 2.31-2.24 (m, 2H), 1.72-1.63 (m, 4H), 1.51-1.45 (m, 3H), 1.42-1.37 (m, 3H).

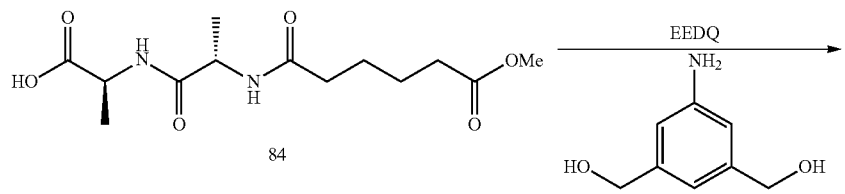

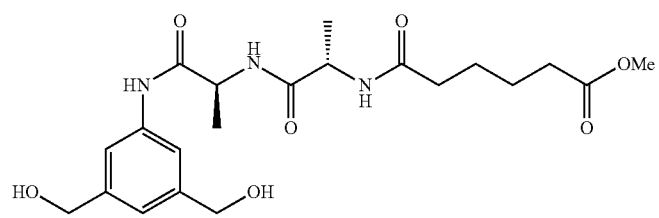

Step 5: Compound 84 (5.6 g, 18.52 mmol) was dissolved in anhydrous dichloromethane (118 mL) and anhydrous methanol (58.8 mL). (5-amino-1,3-phenylene)dimethanol (2.70 g, 17.64 mmol) and EEDQ (8.72 g, 35.3 mmol) were added and the reaction was stirred at room temperature, overnight. The solvent was stripped and ethyl acetate was added. The resulting slurry was filtered, washed with ethyl acetate and dried under vacuum/N₂ to give compound 85 (2.79 g, 36% yield). ¹H NMR (400 MHz, DMSO-d6): δ 9.82 (s, 1H), 8.05, (d, 1H, J=9.2 Hz), 8.01 (d, 1H, J=7.2 Hz), 7.46 (s, 2H), 6.95 (3, 1H), 5.21-5.12 (m, 2H), 4.47-4.42 (m, 4H), 4.40-4.33 (m, 1H), 4.33-4.24 (m, 1H), 3.58 (s, 3H), 2.33-2.26 (m, 2H), 2.16-2.09 (m, 2H), 1.54-1.46 (m, 4H), 1.30 (d, 3H, J=7.2 Hz), 1.22 (d, 3H, J=4.4 Hz).

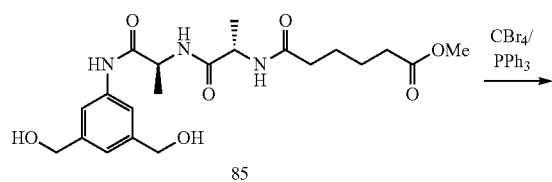

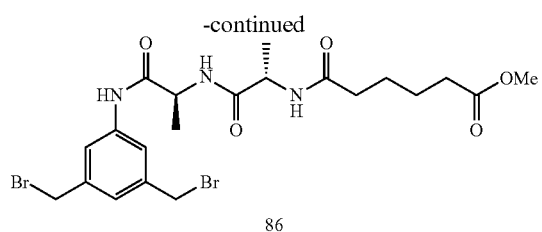

Step 6: Compound 85 (0.52 g, 1.189 mmol) and carbon tetrabromide (1.183 g, 3.57 mmol) were dissolved in anhydrous DMF (11.89 mL). Triphenylphosphine (PPH3) (0.935 g, 3.57 mmol) was added and the reaction stirred under argon for four hours. The reaction mixture was diluted with DCM/MeOH (10:1) and washed with water and brine, dried over sodium sulfate, filtered, and concentrated. The crude material was purified by silica gel chromatography (DCM/MeOH) to give compound 86 (262 mg, 39% yield). ¹H NMR (400 MHz, DMSO-d6): δ 10.01 (s, 1H), 8.11 (d, 1H, J=6.8 Hz), 8.03 (d, 1H, J=6.8 Hz), 7.67 (s, 2H), 7.21 (s, 1H), 4.70-4.64 (m, 4H), 4.40-4.32 (m, 1H), 4.31-4.23 (m, 1H), 3.58 (s, 3H), 2.34-2.26 (m, 2H), 2.18-2.10 (m, 2H), 1.55-1.45 (m, 4H), 1.31 (d, 3H, J=7.2 Hz), 1.21 (d, 3H, J=7.2 Hz).

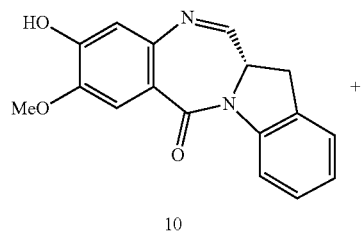

10

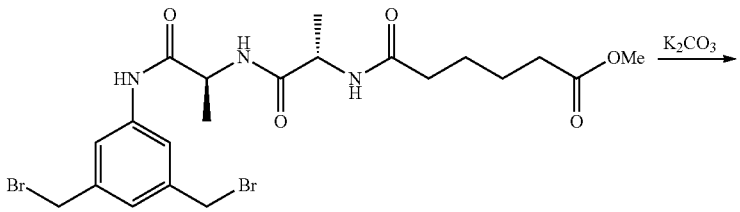

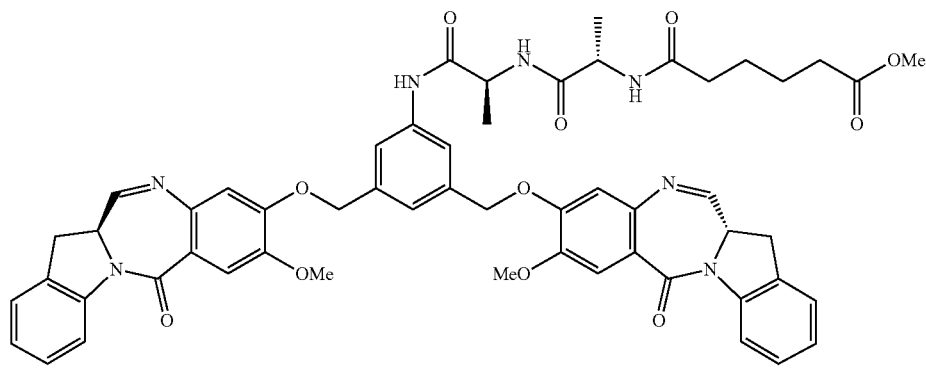

87

Step 7: Dibromide compound 86 and IGN monomer compound 10 were dissolved in DMF (1.84 mL). Potassium carbonate was added and was stirred at room temperature overnight. Water was added to the reaction mixture to precipitate the product. The slurry was stirred at room temperature and was then filtered and dried under vacuum/ $N_2$. The crude material was purified by silica gel chromatography (dichloromethane/methanol) to give compound 87 (336 mg, 74% yield). LCMS=5.91 min (15 min method). MS (m/z): 990.6 (M+1)$^+$.

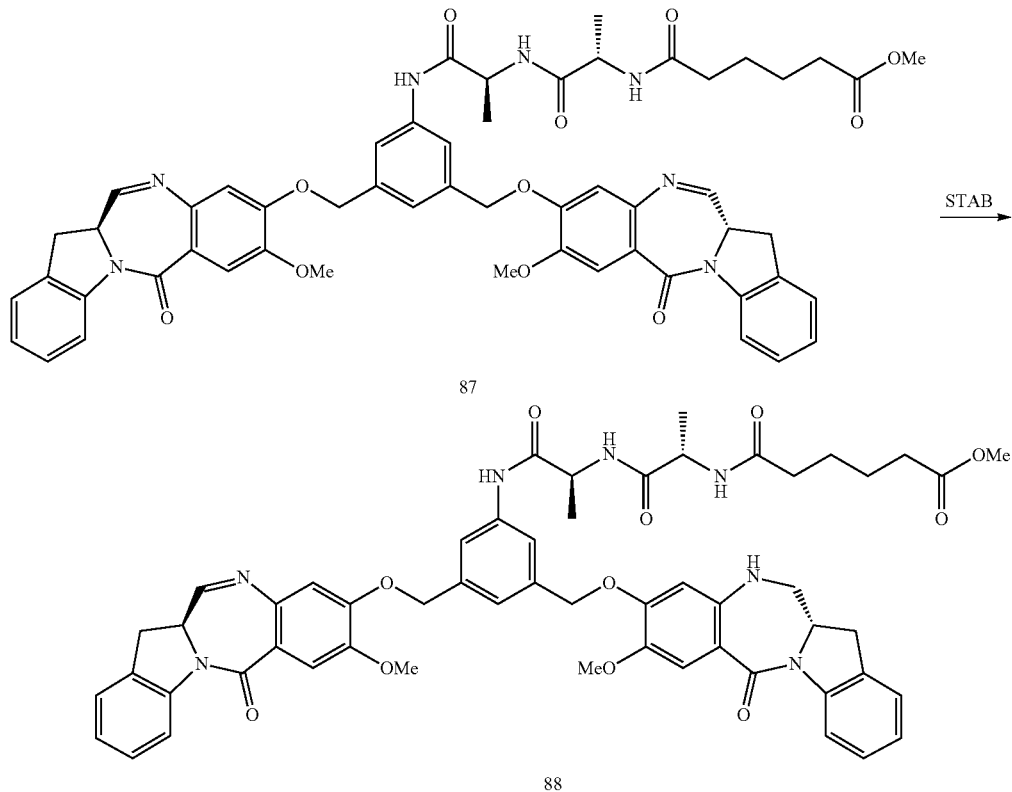

Step 8: Diimine compound 87 was dissolved in 1,2-dichloroethane. NaBH(OAc)$_3$ (STAB) was added to the reaction mixture and was stirred at room temperature for 1 h. The reaction was diluted with CH$_2$Cl$_2$ and was quenched with sat'd aq NH$_4$Cl solution. The layers were separated and was washed with brine, dried over Na$_2$SO$_4$ and concentrated. The crude material was purified via RPHPLC (C18 column, Acetonitrile/Water) to give compound 88 (85.5 mg, 25% yield). LCMS=6.64 min (15 min method). MS (m/z): 992.6 (M+1)$^+$.

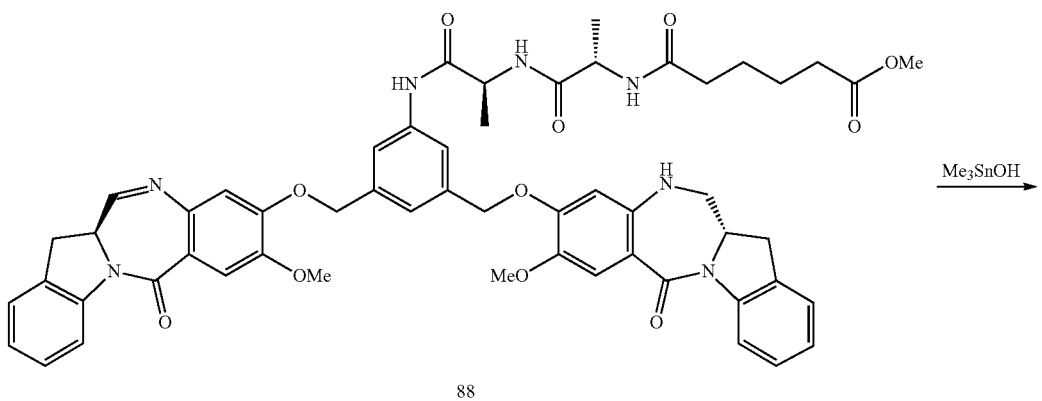

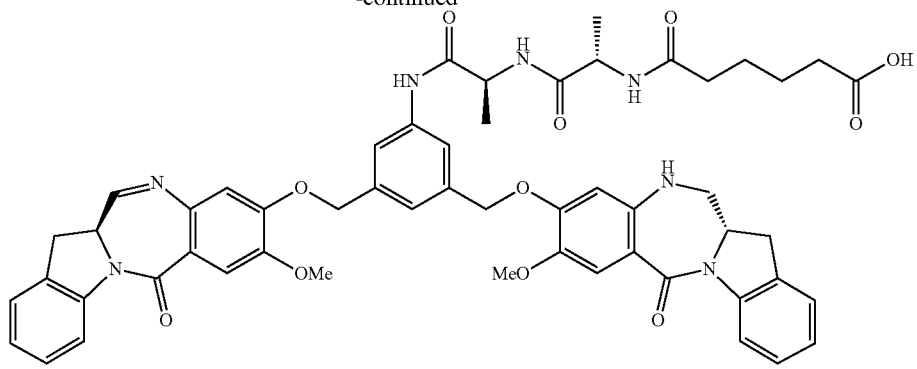

89

Step 9: Methylester compound 88 was dissolved in 1,2-dichloroethane. Trimethylstannanol was added to the reaction mixture and was heated at 80° C. overnight. The reaction mixture was cooled to room temperature and was diluted with water. The aqueous layer was acidified to pH~4 with 1 M HCl. The mixture was extracted with $CH_2Cl_2$/MeOH (10:1, 3×20 mL). The combined organic layers were washed with brine and was dried over $Na_2SO_4$ and concentrated. The crude material was passed through a silica plug to give compound 89 (48.8 mg, 80% yield). LCMS=5.89 min (15 min method). MS (m/z): 978.6 (M+1)$^+$.

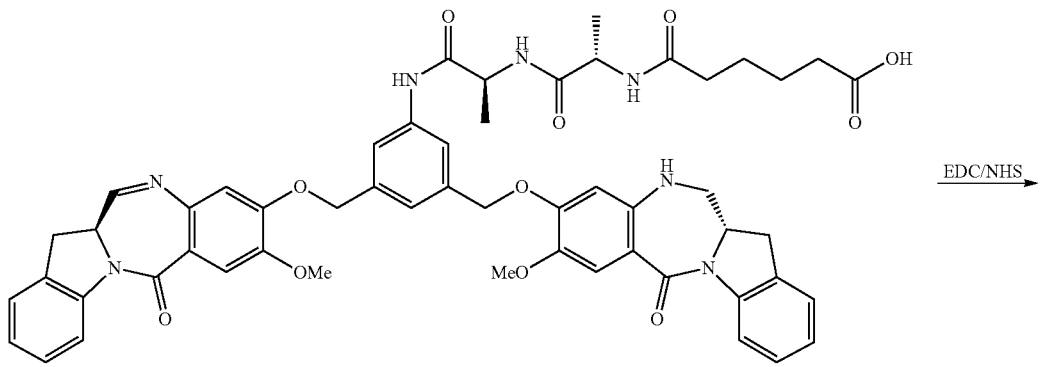

89

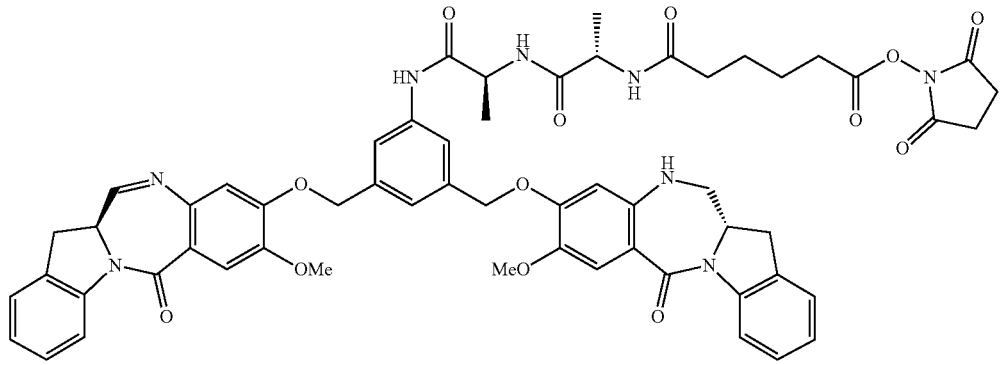

90

Step 10: EDC.HCl was added to a stirred solution of acid compound 89 and N-hydroxysuccinamide in CH$_2$Cl$_2$ at rt. The reaction mixture was stirred for 2 h. The reaction mixture was diluted with CH$_2$Cl$_2$ and was washed with water and brine. The organic layer was dried over Na$_2$SO$_4$, filtered and concentrated. The crude material was purified via RPHPLC (C18 column, Acetonitrile/Water) to give 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((R)-8-methoxy-6-oxo-12a,13-dihydro-6H-benzo[5,6][1,4]diazepino[1,2-a]indol-9-yl)oxy)methyl) phenyl)amino)-1-oxopropan-2-yl)amino)-1-oxopropan-2-yl)amino)-6-oxohexanoate, compound 90 (8.2 mg, 30% yield). LCMS=6.64 min (15 min method). MS (m/z): 1075.4 (M+1)$^+$.

Example 7: Preparation of huMOV19-90

A reaction containing 2.0 mg/mL huMOV19 antibody and 3.9 molar equivalents of compound 90 (pretreated with 5-fold excess of sodium bisulfite in 95:5 DMA:50 mM succinate pH 5.5 for 4 hours at 25° C.) in 15 mM HEPES (4-(2-hydroxyethyl)-1-piperazine ethanesulfonic acid) pH 8.5 buffer and 15% v/v DMA (N,N-Dimethylacetamide) cosolvent was incubated for 4 hours at 25° C. Post-reaction, the conjugate was purified and buffer exchanged into 10 mM succinate, 50 mM sodium chloride, 8.5% w/v sucrose, 0.01% Tween-20, 50 μM sodium bisulfite pH 6.2 formulation buffer using NAP desalting columns (Illustra Sephadex G-25 DNA Grade, GE Healthcare). Dialysis was performed in the same buffer for 4 hours at room temperature and then overnight at 4° C. utilizing Slide-a-Lyzer dialysis cassettes (ThermoScientific 30,000 MWCO).

Figure 6:
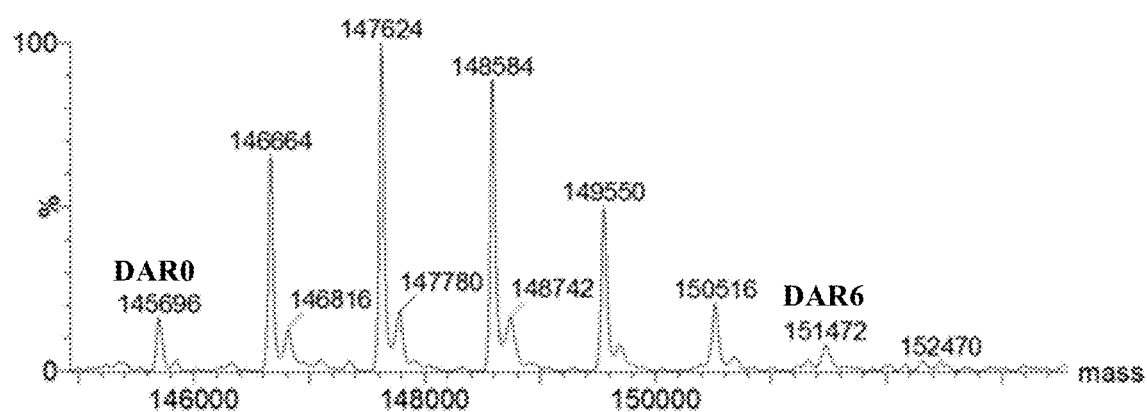
FIG. 6 shows the mass spectrometry data for deglycosylated huMOV19-90 conjugate.

The purified conjugate was found to have a final protein concentration of 1.8 mg/ml and an average of 2.7 molecules of compound 90 linked per antibody (by UV-Vis using molar extinction coefficients $\varepsilon_{330\ nm}$=15,280 cm$^{-1}$M$^{-1}$ and $\varepsilon_{280\ nm}$=30,115 cm$^{-1}$M$^{-1}$ for compound 90, and $\varepsilon_{280\ nm}$=201,400 cm$^{-1}$M$^{-1}$ for huMOV19 antibody); 98.3% monomer (by size exclusion chromatography); and <1.1% unconjugated compound 90 (by acetone precipitation, reverse-phase HPLC analysis). The MS spectrometry data is shown in FIG. 6. DAR0 represents an unconjugated antibody, i.e., an antibody that has no benzodiazepines conjugated to it. DARE represents an antibody with six benzodiazepines linked to it. The peaks in the middle correspond, from left to right, DAR1, DAR2, DAR3, DAR4, and DAR5.

Example 8. Synthesis of Compound 107, Also Referred to Herein as D4

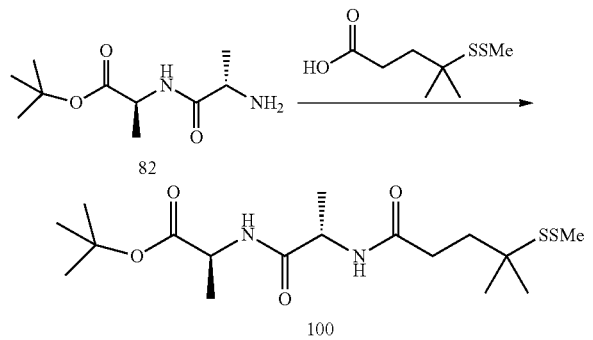

Step 1: Compound 82 (500 mg, 2.31 mmol), 4-methyl-4-(methyldisulfanyl)pentanoic acid (449 mg, 2.31 mmol), EDC.HCl (465 mg, 2.43 mmol), HOBt (354 mg, 2.31 mmol), and DIPEA (0.81 mL, 4.62 mmol) were dissolved in DMF (7.7 mL) and stirred overnight until the reaction was complete. The reaction was diluted with ethyl acetate and washed with saturated sodium bicarbonate, saturated ammonium chloride, and twice with water. The organic was dried and concentrated in vacuo to give compound 100 (875 mg, 96% yield) which was used directly in the next step. $^1$H NMR (400 MHz, DMSO): δ 8.15 (d, 1H, J=6.8 Hz), 8.02 (d, 1H, J=6.8 Hz), 4.26-4.33 (m, 1H), 4.03-4.12 (m, 1H), 2.41 (s, 3H), 2.18-2.22 (m, 2H), 1.76-1.80 (m, 2H), 1.39 (s, 9H), 1.24 (s, 6H), 1.24 (d, 3H, J=7.2 Hz), 1.19 (d, 3H, J=7.2 Hz).

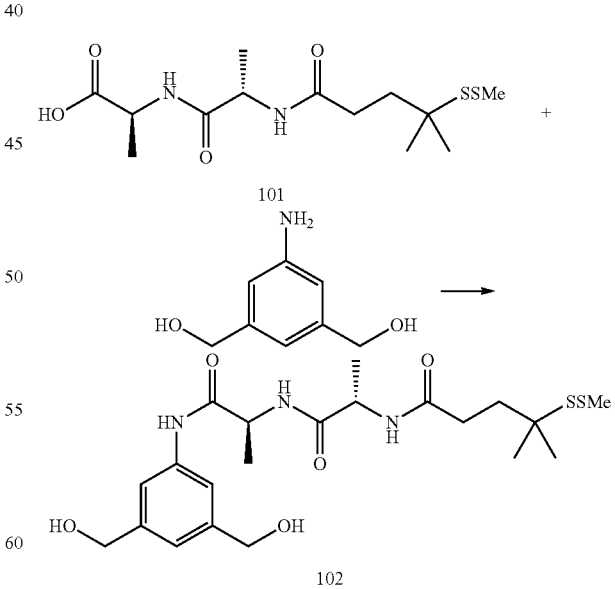

Step 2: TFA (2.6 ml) and water (0.17 ml) were added to neat Compound 100 (875 mg, 2.23 mmol) and were stirred at room temperature until the reaction was complete. The reaction was diluted and azeotroped with acetonitrile to obtain a sticky oil. It was then diluted with acetonitrile and water, frozen and lyophilized to give compound 101 (1 g, 100% yield) as an off white solid that was used without further purification. LCMS=3.99 min (8 min method). MS (m/z): 337.0 (M+1)$^+$.

Step 3: Compound 101 (923 mg, 1.65 mmol) and (5-amino-1,3-phenylene)dimethanol (240 mg, 1.57 mmol) were dissolved in DMF (5.2 ml). EDC.HCl (601 mg, 3.13 mmol), and DMAP (96 mg, 0.78 mmol) were added at room temperature and the reaction was stirred overnight at room temperature. The reaction was diluted with ethyl acetate and washed with water three times. The organic layer was dried, concentrated in vacuo and purified by silica gel chromatography (DCM/MeOH) to give Compound 102 (150 mg, 20% yield). LCMS=3.91 min (8 min method). MS (m/z): 472.2 (M+1)⁺. ¹H NMR (400 MHz, MeOD): δ 9.69 (s, 1H), 8.21 (d, 1H, J=6.8 Hz), 8.18 (d, 1H, J=6.8 Hz), 7.52 (s, 2H), 7.12 (s, 1H), 4.58 (s, 4H), 4.44-4.48 (m, 1H), 4.29-4.32 (m, 1H), 3.34 (s, 2H), 2.38 (s, 3H), 2.34-2.40 (m, 2H), 1.90-1.95 (m, 2H), 1.43 (d, 3H, J=7.2 Hz), 1.36 (d, 3H, J=7.2 Hz), 1.30 (s, 6H).

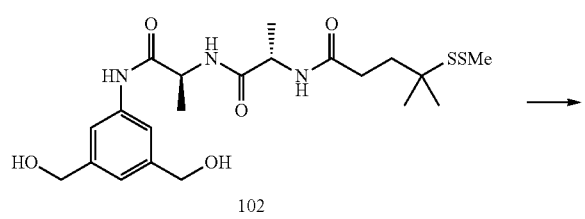

102

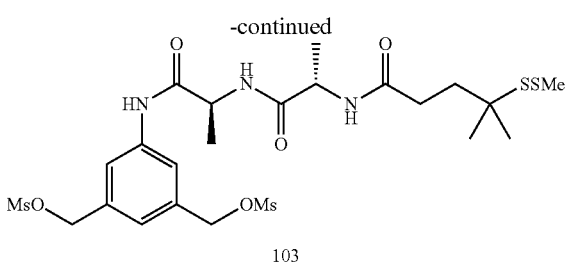

103

Step 4: Compound 102 was suspended in anhydrous DCM. Anhydrous DMF was added until the solution became homogeneous. The solution was cooled to ⁻10° C. in an acetone/dry ice bath. Triethylamine was added, followed by methanesulfonic anhydride. The mixture stirred at ⁻10° C. for 1 hour. The reaction was quenched with ice water and extracted with cold ethyl acetate/methanol (20:1). The organic layer was washed with ice water and dried over anhydrous sodium sulfate, filtered and concentrated. The crude material was dried under high vacuumed to give Compound 103 (174 mgs, 101% yield) that was used directly in the next step without further purification. LCMS=4.95 min (8 min method).

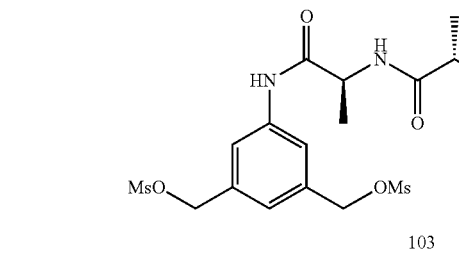

103

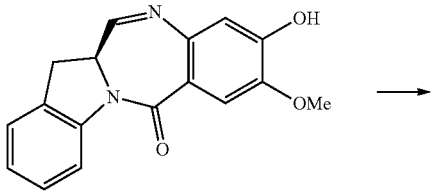

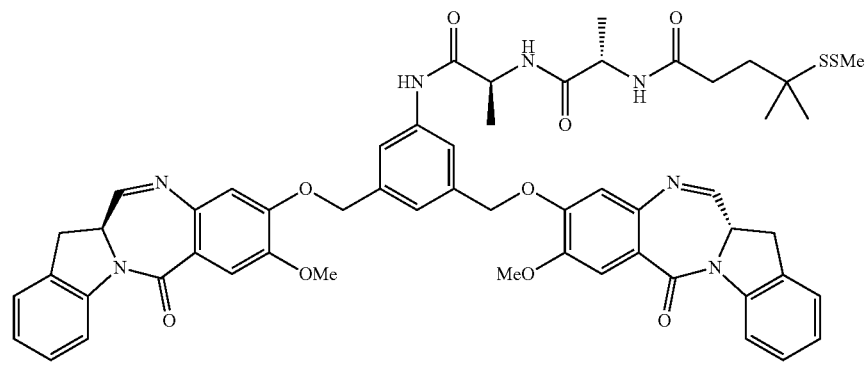

104

Step 5: Dimesylate compound 103 (435 mg, 1.11 mmol) was dissolved in DMF.IGN monomer compound 10 was added, followed by and K$_2$CO$_3$ and was stirred at room temperature under Ar overnight. Water was added to precipitate out the product. The slurry was stirred for 5 min, filtered and dried under vacuum/N$_2$. The crude solid contained compound 104 (203 mg, 44% yield, 60% purity) which was used without further purification. LCMS=5.68 min (8 min method). MS (m/z): 1024.3 (M+1)$^+$.

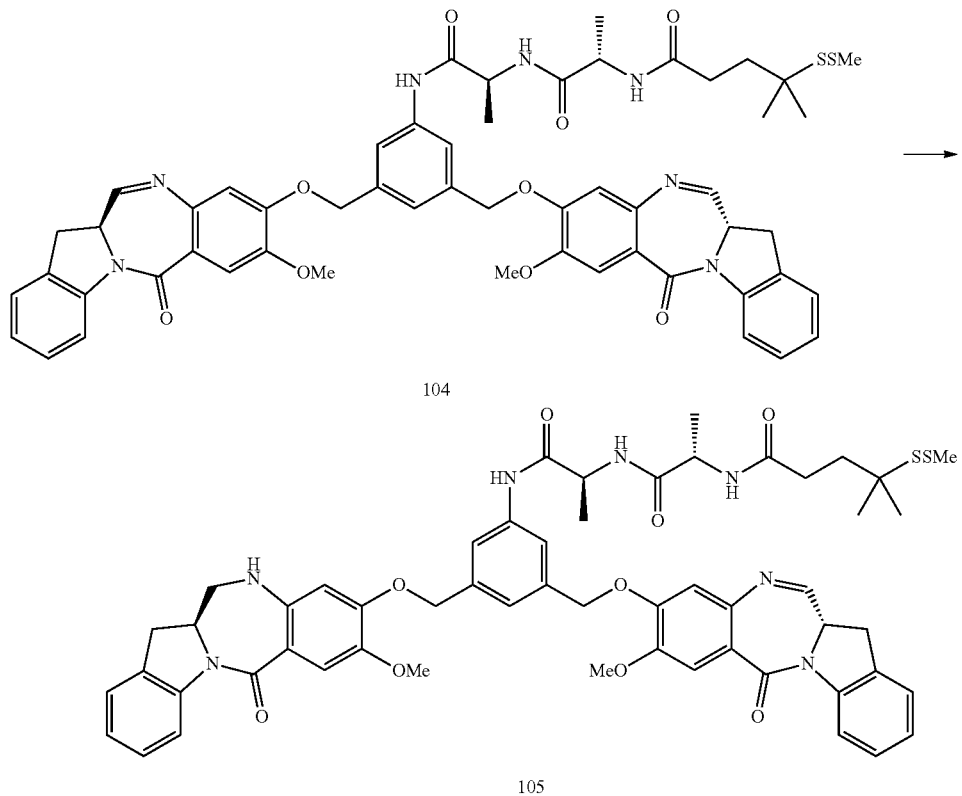

Step 6: Diimine compound 104 was dissolved in 1,2-dichloroethane. NaBH(OAc)$_3$ was added to the reaction mixture and was stirred at rt. The reaction was diluted with CH$_2$Cl$_2$ and was quenched with sat'd aq NH$_4$Cl solution (15 mL). The layers were separated and was washed with brine, dried over Na$_2$SO$_4$ and concentrated. The crude residue was purified by RPHPLC (C18 column, CH$_3$CN/H$_2$O, gradient, 50% to 65%) to yield mono imine compound 105 as a solid (22 mg, 16% yield, 90% pure). LCMS=6.00 min (8 min method). MS (m/z): 1027.3 (M+1)$^+$.

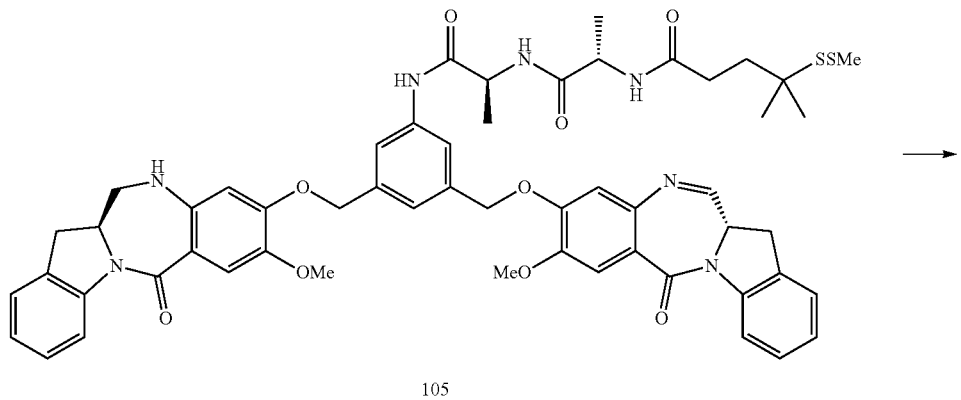

-continued

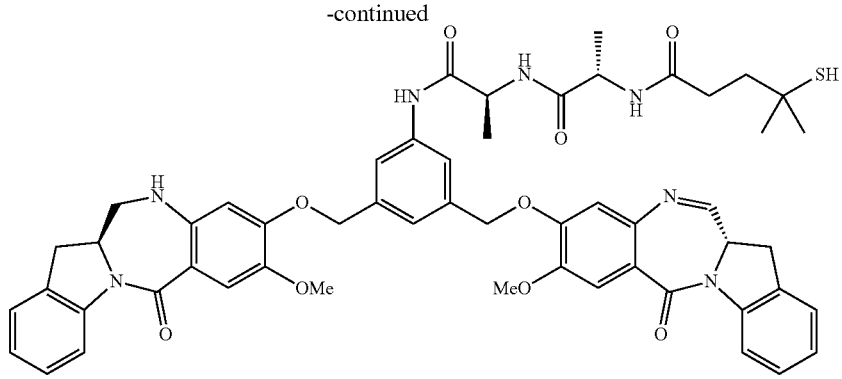

106

Step 7: Compound 106 was dissolved in THF (0.5 mL) and ACN (0.23 mL) at room temperature. It was then prepared similarly to compound 98 in Example 9. The mixture was stirred until completion and then diluted with DCM and DI water. The organic layer was washed with brine, dried and filtered. The filtrate was concentrated to give the crude thiol, compound 106 (21 mg, 100% yield) which was used directly in the next reaction. LCMS=5.67 min (8 min method). MS (m/z): 980.4 (M+1)$^+$.

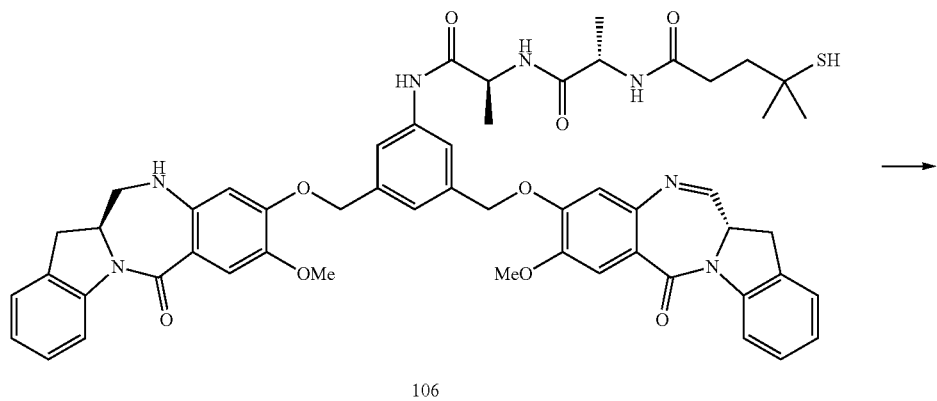

106

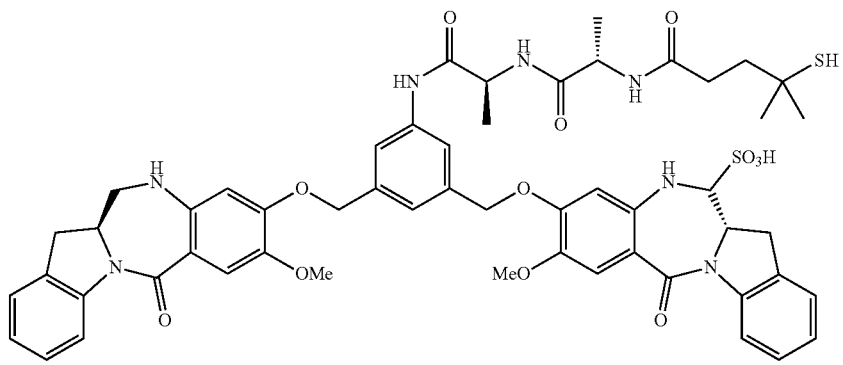

107

Step 8: Compound 106 (21 mg, 0.021 mmol) was suspended in 2-propanol (1428 µl) and water (714 µl). Sodium metabisulfite (22.30 mg, 0.214 mmol) was added and the reaction stirred at room temperature until completion. The reaction mixture was diluted with acetonitrile/water, frozen and lyophilized. The resulting white powder was purified by RPHPLC (C18 column, $CH_3CN/H_2O$, gradient, 20% to 40%) and the desired fractions were collected and lyophilized to give compound 107 (5.3 mg, 23% yield). LCMS=5.67 min (8 min method). MS (m/z): 1060.2 $(M-1)^-$.

Example 9. Preparation of huMOV19-Sulfo-SPDB-107 (or huMOV19-107) Conjugate

An in situ mix containing final concentrations of 1.95 mM Compound 107 and 1.5 mM sulfo-SPDB Linker in succinate buffer (pH 5): DMA (30:70) was incubated for 6 h before adding a 7-fold excess of 107-sulfo-SPDB-NHS to a reaction containing 4 mg/ml huMOV19 antibody in 15 mM HEPES pH 8.5 (87:13, water: DMA). The solution was allowed to conjugate over night at 25° C.

Post-reaction, the conjugate was purified and buffer exchanged into 10 mM Tris, 80 mM NaCl, 50 uM Bisulfite, 3.5% Sucrose, 0.01% Tween-20 formulation buffer pH 7.6 using NAP desalting columns (Illustra Sephadex G-25 DNA Grade, GE Healthcare). Dialysis was performed in the same buffer over night at 4° C. utilizing Slide-a-Lyzer dialysis cassettes (ThermoScientific 10,000 MWCO).

Figure 7:
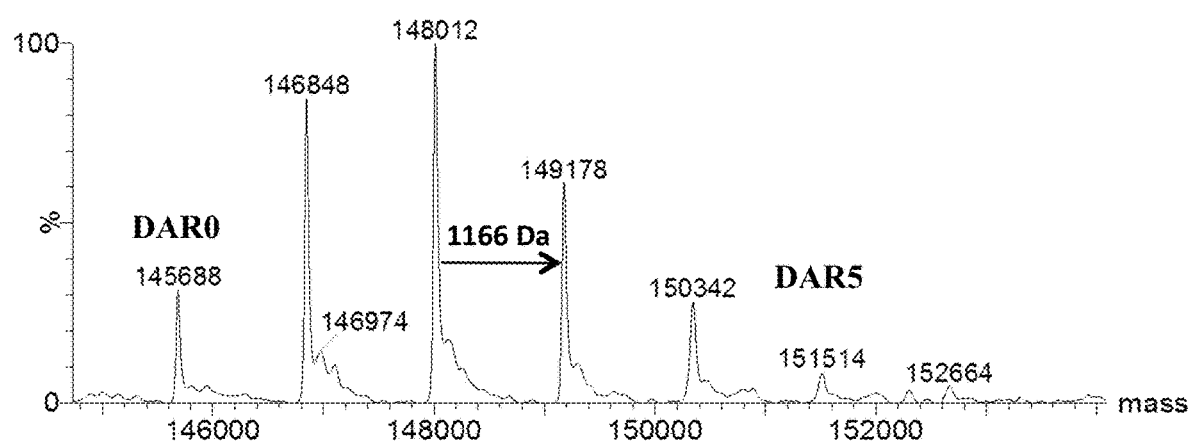
FIG. 7 shows the mass spectrometry data for deglycosylated huMov19-sSPDB-107 conjugate.

The purified conjugate was found to have an average of 2.7 molecules of compound 107 linked per antibody (by UV/Vis and SEC using molar extinction coefficients $\varepsilon_{330\ nm}=15,484\ cm^{-1}M^{-1}$ and $\varepsilon_{280\ nm}=30,115\ cm^{-1}M^{-1}$ for compound 107, and $\varepsilon_{280\ nm}=201,400\ cm^{-1}M^{-1}$ for huMOV19 antibody), 95% monomer (by size exclusion chromatography), and a final protein concentration of 1.1 mg/ml. The MS spectrometry data is shown in FIG. 7. DAR0 represents an unconjugated antibody, i.e., an antibody that has no benzodiazepines conjugated to it. DAR5 represents an antibody with five benzodiazepines linked to it. The peaks in the middle correspond, from left to right, DAR1, DAR2, DAR3, and DAR4.

Example 10. Reduced RSA with Low pH Succinate Buffers

This example demonstrates the production of compositions that reduce, inhibit, or eliminate reversible self-association where the compositions include a conjugate comprising an antibody with an engineered cysteine (e.g., a non-naturally occurring cysteine introduced into the antibody heavy chain or light chain in place of another non-cysteine amino acid) chemically coupled to an indolinobenzodiazepine, buffering agent, surfactant, sugar, and water.

Conjugates comprising the AbX monoclonal antibody chemically coupled to the indolinobenzodiazepine D2(a) through engineered cysteines were produced. The conjugates were formulated as (a) 10 mM histidine, 8% trehalose, 0.01% polysorbate 20, pH 5.5; or (b) 10 mM sodium succinate, 8% trehalose, 0.01% polysorbate 20, pH 4.2.

Figure 8:
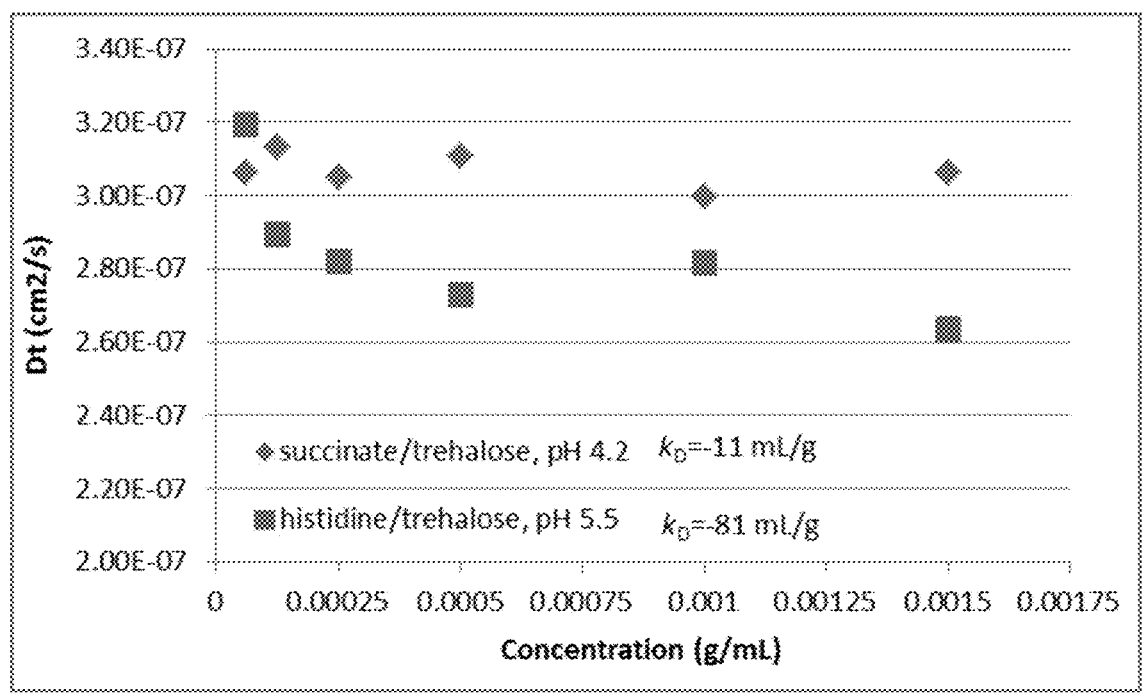
FIG. 8 shows the dynamic light scattering plot of different ADC compositions.

As shown in FIG. 8, the succinate and trehalose combination at pH 4.2 (formula (b)) showed a greater reduction in reversible self-association as measured by DLS when compared to the histidine trehalose combination (formula (a)).

These results demonstrate the ability of compositions disclosed herein to reduce, inhibit, or eliminate reversible self-association at lower pH ranges such as pH 4.2.

Example 11. Reduced RSA with Succinate Buffer

This example demonstrates the production of compositions that reduce, inhibit, or eliminate reversible self-association comprising a conjugate comprising an antibody chemically coupled to an indolinobenzodiazepine, succinate-based buffering agent, surfactant, sugar, and water.

Conjugates comprising the huMy-9-6 monoclonal antibody chemically coupled to the indolinobenzodiazepine DGN462 via a 4-(2-pyridinyldithio)-2-sulfo-,1-(2,5-dioxo-1-pyrrolidinyl) butanoic acid ester (sSPDB) linker ("huMy-9-6-sSPDB-DGN462") were prepared using methods described herein and known in the art (see, e.g., U.S. Pat. No. 6,441,163). The huMy-9-6-sSPDB-DGN462 conjugate was formulated as follows: (a) 20 mM histidine, 8% trehalose, 0.02% polysorbate 20, pH 6.1; (b) 10 mM acetate, 8% trehalose, pH 4.2; and (c) 10 mM sodium succinate, 8% trehalose, pH 4.2.

Figure 9:
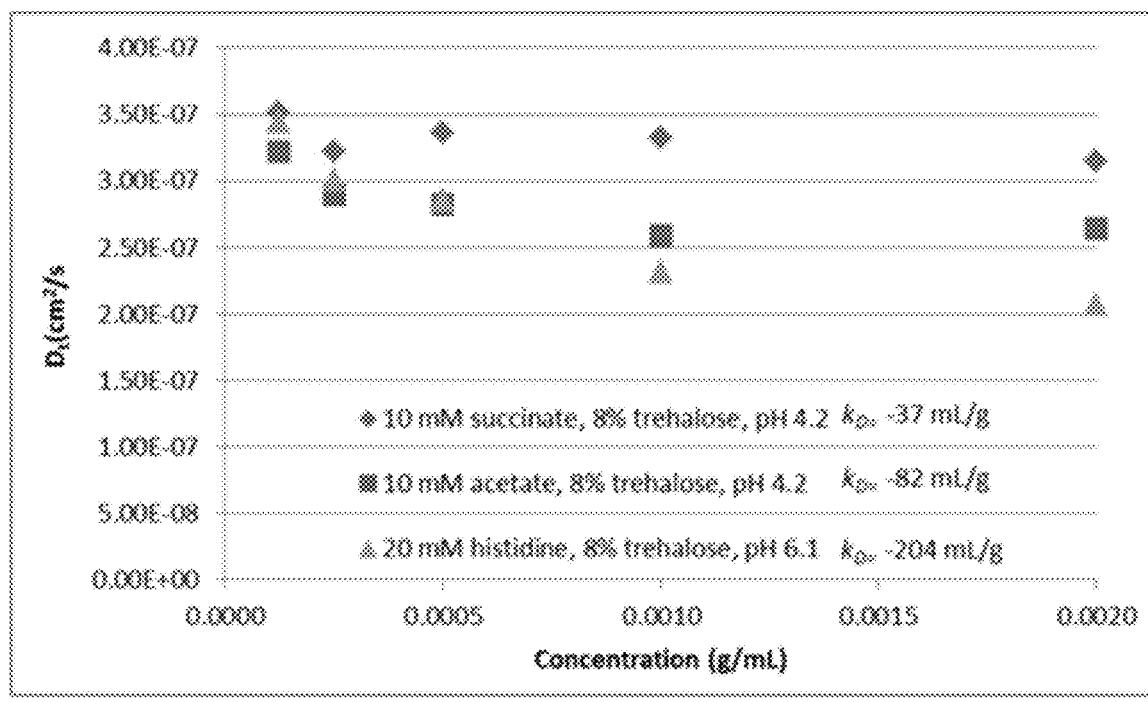
FIG. 9 shows the dynamic light scattering plot of different ADC compositions.

The results of analysis by dynamic light scattering demonstrating the effects of the formulation pH and buffering agent on reversible self-association are set forth in FIG. 9. These results indicate that succinate (formula (c)) as a buffering agent is more effective at reducing reversible self-association than acetate (formula (b)) in the pH range of 4.0 to 4.5, and both are more effective than histidine (formula (a)) at pH 6.1.

As also shown in FIG. 9, the succinate trehalose combination (formula (c)) is more effective than the acetate trehalose combination (formula (b)) at reducing reversible self-association at pH 4.2.

Figure 10:
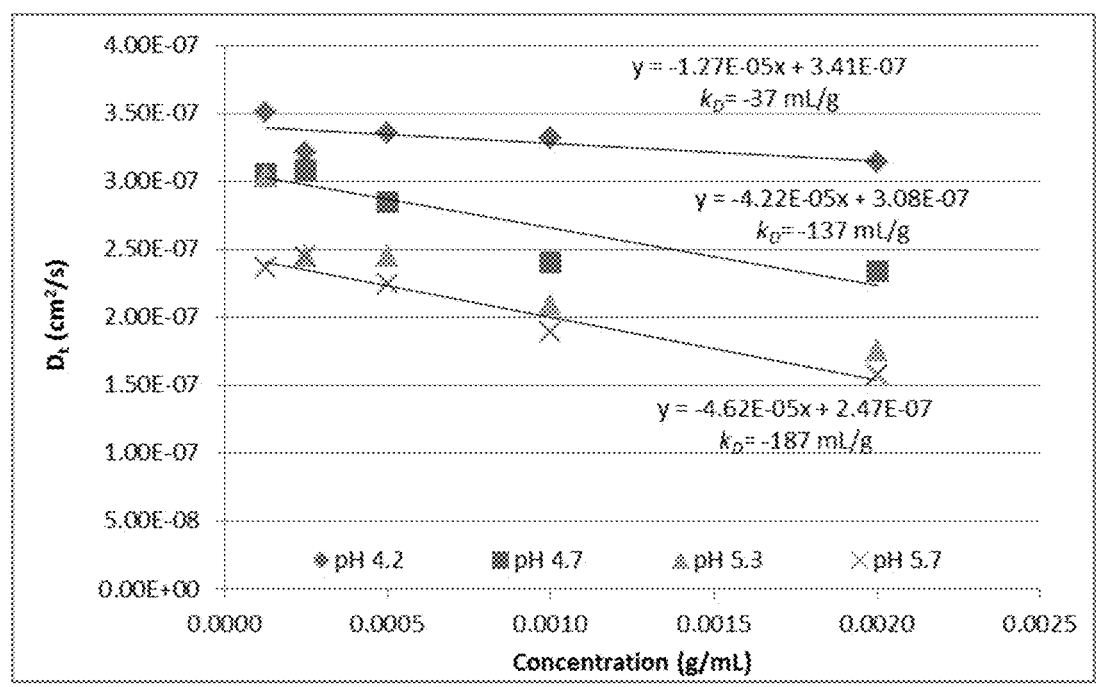
FIG. 10 shows data obtained from an assessment of RSA for a succinate-trehalose formulation over a range of pH.

In addition, the data shown in FIG. 10 result from the assessment of reversible self-association for the succinate-trehalose combination over the range of pH4.2 to pH5.7. The results show that reduction in reversible self-association increases as the pH decreases, as shown herein with the use of a succinate buffer.

Example 12. Reduced RSA with Low pH Succinate Buffers

This example demonstrates the production of compositions that reduce, inhibit, or eliminate reversible self-association where the compositions include a conjugate comprising an antibody with an engineered cysteine (e.g., a non-naturally occurring cysteine introduced into the antibody heavy chain or light chain in place of another non-cysteine amino acid) chemically coupled to an indolinobenzodiazepine, buffering agent, surfactant, sugar, and water.

Conjugates comprising the AbX monoclonal antibody chemically coupled to the indolinobenzodiazepine D2(a) through engineered cysteines were produced. The conjugate was formulated as 10 mM sodium succinate, 8% trehalose, 0.01% polysorbate 20, pH 4.0.

Figure 11:
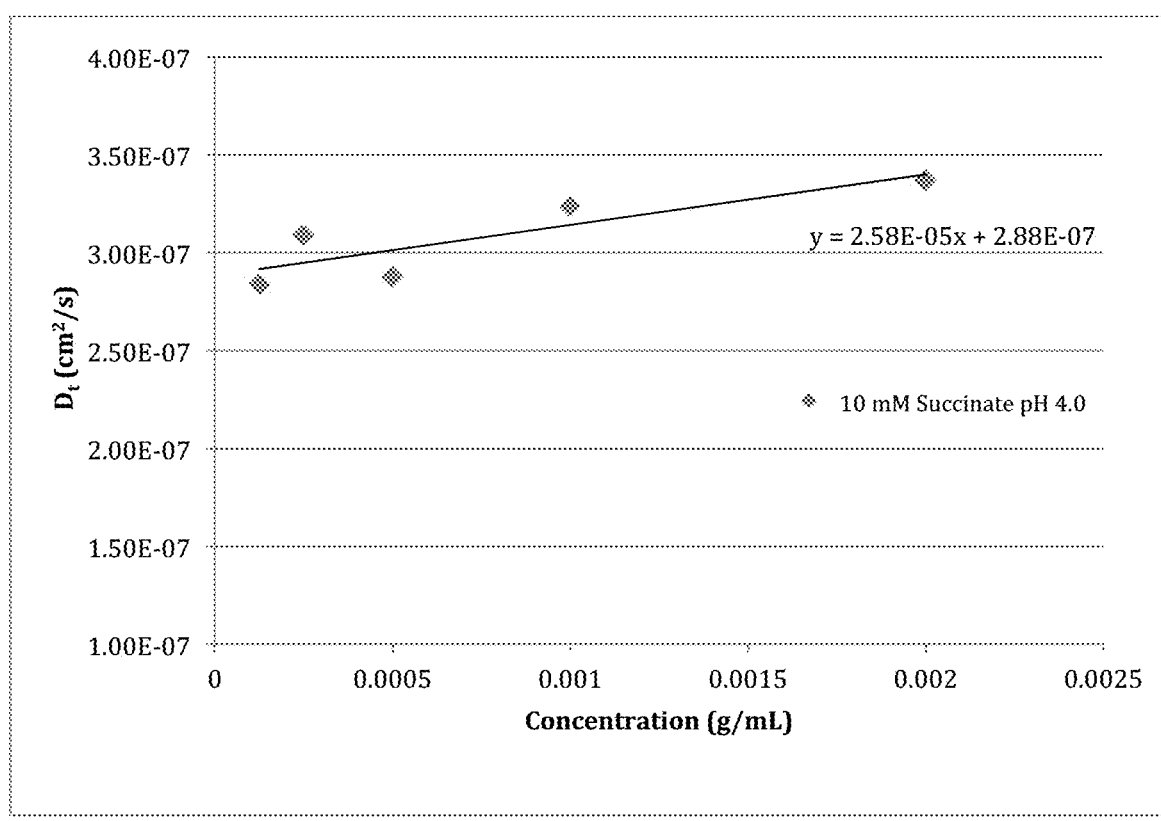
FIG. 11 shows RSA of ADC in 10 mM Sodium succinate, 8% trehalose, 0.01% Polysorbate-20, pH 4.0

As shown in FIG. 11, the succinate and trehalose combination at pH 4.0 showed an equivalent or greater reduction in reversible self-association as measured by DLS when compared to the succinate/trehalose formulation at pH 4.2.

Using a site-specific conjugate, this example shows the reduction of RSA even in a conjugate with a lower DAR. These results further demonstrate the ability of compositions disclosed herein to reduce, inhibit, or eliminate reversible self-association particularly at lower pH ranges such as pH 4.0-4.5, even for site specific conjugates with a DAR of, for example, 2.0.

EQUIVALENTS

It is to be understood that the foregoing description is intended to illustrate and not limit the scope of the invention, which is defined by the scope of the appended claims. Those skilled in the art will recognize, or be able to ascertain, using no more than routine experimentation, numerous equivalents to the specific embodiments described specifically in this disclosure. Such equivalents, and other aspects, advantages, and modifications are within the scope of the following claims.

The invention claimed is:

1. An aqueous formulation comprising:
   (a) water;
   (b) about 2 mg/mL of a conjugate of the following formulae:

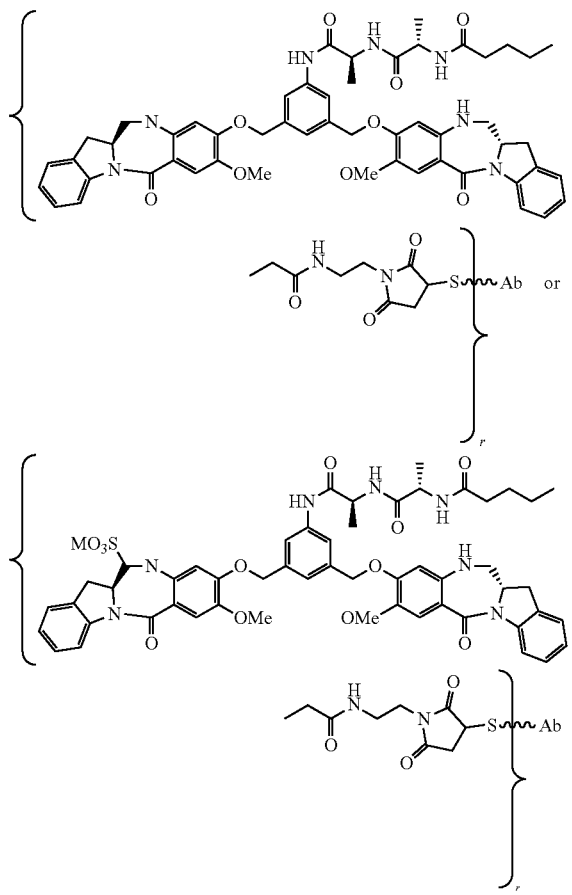

(c) 10 mM sodium succinate; and
   (d) 8% trehalose dihydrate;
      wherein Ab is an antibody, or antigen-binding fragment thereof, that binds to CD123 and comprises a heavy chain variable region (VH) complementarity determining region (CDR1) sequence of SEQ ID NO: 1, a VH CDR2 sequence of SEQ ID NO: 2, and a VH CDR3 sequence of SEQ ID NO: 3 and a light chain variable region (VL) CDR1 sequence of SEQ ID NO: 4, a VL CDR2 sequence of SEQ ID NO: 5, and a VL CDR3 sequence of SEQ ID NO: 6;
   wherein M is $H^+$, $Na^+$, $K^+$, or any pharmaceutically acceptable cation;
   wherein r is an integer from 1 to 10; and
   wherein the formulation has a pH ranging from about 4.0 to about 4.5.

2. The aqueous formulation of claim 1, wherein the antibody or antigen-binding fragment thereof comprises a heavy chain variable region at least about 90% identical to SEQ ID NO: 7 and a light chain variable region at least about 90% identical to SEQ ID NO: 9.

3. The aqueous formulation of claim 1, wherein the antibody or antigen-binding fragment thereof comprises a heavy chain at least about 90% identical to SEQ ID NO: 11 and a light chain at least about 90% identical to SEQ ID NO: 14.

4. The aqueous formulation of claim 1, wherein the antibody or antigen-binding fragment thereof comprises a heavy chain at least about 90% identical to SEQ ID NO: 12 and a light chain at least about 90% identical to SEQ ID NO: 14.

5. The formulation of claim 4, further comprising 0.01% polysorbate 20.

6. The formulation of claim 5, wherein the pH is about 4.2.

7. The formulation of claim 6, further comprising between about 2 µM and about 200 µM sodium bisulfite.

8. The formulation of claim 7, further comprising about 50 µM sodium bisulfite.

9. The aqueous formulation of claim 4, further comprising about 0.005% and about 0.1% polysorbate 20.

10. The aqueous formulation of claim 1, wherein the antibody or antigen-binding fragment thereof comprises a heavy chain variable region at least about 95% identical to SEQ ID NO: 7 and a light chain variable region at least about 95% identical to SEQ ID NO: 9.

11. The aqueous formulation of claim 1, wherein the antibody or antigen-binding fragment thereof comprises a heavy chain variable region comprising the sequence of SEQ ID NO: 7 and a light chain variable region comprising the sequence of SEQ ID NO: 9.

12. The aqueous formulation of claim 1, wherein the antibody or antigen-binding fragment thereof comprises a heavy chain amino acid sequence at least about 95% identical to SEQ ID NO: 11 and a light chain amino acid sequence at least about 95% identical to SEQ ID NO: 14.

13. The aqueous formulation of claim 1, wherein the antibody or antigen-binding fragment thereof comprises a heavy chain amino acid sequence comprising the sequence of SEQ ID NO: 11 and a light chain amino acid sequence comprising the sequence of SEQ ID NO: 14.

14. The aqueous formulation of claim 1, wherein the antibody or antigen-binding fragment thereof comprises a heavy chain amino acid sequence at least about 95% identical to SEQ ID NO: 12 and a light chain amino acid sequence at least about 95% identical to SEQ ID NO: 14.

15. The aqueous formulation of claim 1, wherein the antibody or antigen-binding fragment thereof comprises a heavy chain amino acid sequence comprising the sequence of SEQ ID NO: 12 and a light chain amino acid sequence comprising the sequence of SEQ ID NO: 14.

16. The aqueous formulation of claim 1, wherein the conjugate has a drug to antibody ratio of between about 1 and about 2.

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Ile Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ile Lys Pro Tyr Asn Asp Gly Thr Lys Tyr Asn Glu Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Gly Gly Asn Asp Tyr Tyr Asp Thr Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Asp Ile Asn Ser Tyr Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Val Asn Arg Leu Val Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Tyr Asp Ala Phe Pro Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Phe or Val

<400> SEQUENCE: 7

Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120

<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Gly Phe Thr Ser Ser
            20                  25                  30

Ile Met His Trp Val Arg Gln Ala Pro Gly Gln Gly Leu Glu Trp Met
        35                  40                  45

Gly Tyr Ile Lys Pro Tyr Asn Asp Gly Thr Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

```
Gln Gly Thr Leu Val Thr Val Ser Ser
        115                 120
```

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105
```

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ala Trp Phe Gln Gln Lys Pro Gly Lys Ala Pro Lys Ser Leu Ile
        35                  40                  45

Tyr Arg Val Asn Arg Leu Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105
```

<210> SEQ ID NO 11
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)

<223> OTHER INFORMATION: Phe or Val

<400> SEQUENCE: 11

```
Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 12
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Phe or Val

<400> SEQUENCE: 12

Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Cys Leu Ser
        435                 440                 445

Pro Gly
    450

<210> SEQ ID NO 13
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Gly Phe Thr Ser Ser
            20                  25                  30

Ile Met His Trp Val Arg Gln Ala Pro Gly Gln Gly Leu Glu Trp Met
        35                  40                  45

Gly Tyr Ile Lys Pro Tyr Asn Asp Gly Thr Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 14
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ala Trp Phe Gln Gln Lys Pro Gly Lys Ala Pro Lys Ser Leu Ile
        35                  40                  45

Tyr Arg Val Asn Arg Leu Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```